(12) United States Patent
Barnes et al.

(10) Patent No.: US 12,247,230 B2
(45) Date of Patent: *Mar. 11, 2025

(54) MUTANT POLYMERASES AND USES THEREOF

(71) Applicant: DNA POLYMERASE TECHNOLOGY, INC., St. Louis, MO (US)

(72) Inventors: Wayne M. Barnes, University City, MO (US); Milko B. Kermekchiev, St. Louis, MO (US); Zhian Zhang, Ballwin, MO (US)

(73) Assignee: DNA POLYMERASE TECHNOLOGY, INC., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/476,104

(22) Filed: Sep. 27, 2023

(65) Prior Publication Data
US 2024/0026315 A1 Jan. 25, 2024

Related U.S. Application Data

(63) Continuation of application No. 17/303,445, filed on May 28, 2021, now Pat. No. 11,814,655, which is a continuation of application No. 15/572,693, filed as application No. PCT/US2016/032041 on May 12, 2016, now Pat. No. 11,091,745.

(60) Provisional application No. 62/160,404, filed on May 12, 2015.

(51) Int. Cl.
C12N 9/12 (2006.01)
C12N 15/10 (2006.01)
C12Q 1/6844 (2018.01)

(52) U.S. Cl.
CPC ......... *C12N 9/1252* (2013.01); *C12N 9/1276* (2013.01); *C12N 15/1096* (2013.01); *C12Q 1/6846* (2013.01); *C12Y 207/07007* (2013.01); *C12Y 207/07049* (2013.01); *C12Q 2521/101* (2013.01); *C12Q 2531/101* (2013.01); *C12Q 2531/119* (2013.01)

(58) Field of Classification Search
None
See application file for complete search history.

(56) References Cited

U.S. PATENT DOCUMENTS

| | | | |
|---|---|---|---|
| 5,408,038 A | 4/1995 | Smith et al. | |
| 5,436,149 A | 7/1995 | Barnes | |
| 5,436,326 A | 7/1995 | Ishino et al. | |
| 5,501,963 A | 3/1996 | Burckhardt | |
| 5,616,494 A | 4/1997 | Barnes | |
| 5,753,482 A | 5/1998 | Ishino et al. | |
| 5,928,866 A | 7/1999 | Imamoto et al. | |
| 6,210,885 B1 | 4/2001 | Gjerde et al. | |
| 6,395,526 B1 | 5/2002 | Uemori et al. | |
| 6,403,341 B1 | 6/2002 | Barnes et al. | |
| 6,410,277 B1 | 6/2002 | Barnes | |
| 6,448,048 B1 | 9/2002 | Tomono et al. | |
| 6,818,431 B1 | 11/2004 | Hong et al. | |
| 7,179,590 B2 | 2/2007 | Smith et al. | |
| 7,211,647 B2 | 5/2007 | Ishino et al. | |
| 7,393,635 B2 | 7/2008 | Barnes | |
| 7,462,475 B2 | 12/2008 | Kermekchiev et al. | |
| 7,514,210 B2 | 4/2009 | Holliger et al. | |
| 7,820,423 B2 | 10/2010 | Doi et al. | |
| 7,927,853 B2 | 4/2011 | Nishida et al. | |
| 8,003,346 B2 | 8/2011 | Tokida et al. | |
| 8,470,563 B2 | 6/2013 | Kermekchiev et al. | |
| 8,481,685 B2 | 7/2013 | Bourn et al. | |
| 9,096,835 B2 | 8/2015 | Holliger et al. | |
| 9,447,388 B2 | 9/2016 | Ishino et al. | |
| 9,796,965 B2 | 10/2017 | Kermekchiev et al. | |
| 9,896,671 B2 | 2/2018 | Ignatov et al. | |
| 10,457,968 B2 | 10/2019 | Bourn et al. | |
| 10,662,413 B2 | 5/2020 | Lin Wu et al. | |
| 10,683,537 B2 | 6/2020 | Kermekchiev et al. | |
| 2003/0228616 A1 | 12/2003 | Arezi et al. | |
| 2004/0005594 A1 | 1/2004 | Holliger et al. | |
| 2004/0081963 A1 | 4/2004 | Wang | |
| 2004/0161767 A1 | 8/2004 | Baldwin et al. | |
| 2005/0250131 A1 | 11/2005 | Jestin et al. | |
| 2005/0260606 A1 | 11/2005 | Kermekchiev et al. | |
| 2006/0084074 A1 | 4/2006 | Kermekchiev et al. | |
| 2007/0020622 A1 | 1/2007 | Lee et al. | |
| 2007/0048748 A1 | 3/2007 | Wiliams et al. | |
| 2007/0111234 A1 | 5/2007 | Birkner et al. | |

(Continued)

FOREIGN PATENT DOCUMENTS

| | | |
|---|---|---|
| CN | 103266103 A | 8/2013 |
| JP | 2009136188 A | 6/2009 |

(Continued)

OTHER PUBLICATIONS

Barnes et al., "A Single Amino Acid Change to Taq DNA Polymerase Enables Faster PCR, Reverse Transcription and Strand-Displacement," Frontiers in Bioengineering and Biotechnology, Jan. 2021, vol. 8, Article 553474, 10 pages.

(Continued)

Primary Examiner — Richard G Hutson
(74) Attorney, Agent, or Firm — McKee, Voorhees & Sease, PLC

(57) ABSTRACT

Provided are mutant polymerases having DNA polymerase activity and reverse transcriptase activity or strand displacement activity, along with target nucleic acid amplification methods employing such mutant polymerases.

15 Claims, 23 Drawing Sheets

Specification includes a Sequence Listing.

(56) References Cited

U.S. PATENT DOCUMENTS

| | | |
|---|---|---|
| 2008/0014609 A1 | 1/2008 | Jestin et al. |
| 2008/0166772 A1 | 7/2008 | Hollinger et al. |
| 2009/0170060 A1 | 7/2009 | Kermekchiev et al. |
| 2010/0013291 A1 | 1/2010 | Baladi |
| 2011/0027832 A1 | 2/2011 | Kermekchiev et al. |
| 2011/0027833 A1 | 2/2011 | Hogrefe et al. |
| 2011/0142792 A1 | 6/2011 | Kahre et al. |
| 2011/0281305 A1 | 11/2011 | Bourn et al. |
| 2012/0028259 A1 | 2/2012 | Zhang et al. |
| 2012/0094332 A1 | 4/2012 | Lee et al. |
| 2013/0034879 A1 | 2/2013 | Skirgaila et al. |
| 2013/0040365 A1 | 2/2013 | Vander Horn et al. |
| 2013/0209473 A1 | 8/2013 | de Sauvage et al. |
| 2014/0113299 A1 | 4/2014 | Kermekchiev et al. |
| 2014/0186840 A1 | 7/2014 | Ding et al. |
| 2014/0322793 A1 | 10/2014 | Ishino et al. |
| 2014/0363875 A1 | 12/2014 | Ishino et al. |
| 2016/0304845 A1 | 10/2016 | Ishino et al. |
| 2021/0147908 A1 | 5/2021 | Kermekchiev et al. |

FOREIGN PATENT DOCUMENTS

| | | |
|---|---|---|
| WO | 9206200 A1 | 4/1992 |
| WO | 2004013279 A2 | 2/2004 |
| WO | 2005113829 A2 | 12/2005 |
| WO | 2009049630 A1 | 4/2009 |
| WO | 2009108693 A2 | 9/2009 |
| WO | 2010062777 A2 | 6/2010 |
| WO | 2010062779 A2 | 6/2010 |
| WO | 2012088479 A2 | 6/2012 |
| WO | 2012110061 A1 | 8/2012 |
| WO | 2014181875 A1 | 11/2014 |

OTHER PUBLICATIONS

Betts et al., "Amino Acid Properties and Consequence of Substitutions," Bioinformatics for Geneticists, John Wiley & Sons, Ltd., 2003, pp. 289-316.

Final Office Action in U.S. Appl. No. 16/901,101, mailed Jun. 16, 2022, 56 pages.

French et al., "What is a Conservative Substitution?" Journal of Molecular Evolution, 1983, vol. 19, pp. 171-175.

Third-Party Submission Under 37 CFR 1.290 Concise Description of Relevance in U.S. Appl. No. 16/901,101, Jun. 9, 2021, 22 pages.

Akane, A., et al., "Identification of the Heme Compound Copurified with Deoxyribonucleic Acid (DNA) from Bloodstains, a Major Inhibitor of Polymerase Chain Reaction (PCR) Amplification," Journal of Forensic Sciences, vol. 39, Issue 2, pp. 362-372, 1994.

Al-Soud, W. A., et al., "A Sample Preparation Method Which Facilitates Detection of Bacteria in Blood Cultures by the Polymerase Chain Reaction," Journal of Microbiological Methods, vol. 32, pp. 217-224, 1998.

Al-Soud, W. A., et al., "Capacity of Nine Thermostable DNA Polymerases to Mediate DNA Amplification in the Presence of PCR-inhibiting Samples," Applied and Environmental Microbiology, vol. 64, No. 10, pp. 3748-3753, Oct. 1998.

Al-Soud, W. A., et al., "Effects of Amplification Facilitators on Diagnostic PCR in the Presence of Blood, Feces, and Meat," Journal of Clinical Microbiology, vol. 38, No. 12, pp. 4463-4470, Dec. 2000.

Al-Soud, W. A., et al., "Identification and Characterization of Immunoglobulin G in Blood as a Major Inhibitor of Diagnostic PCR," Journal of Clinical Microbiology, vol. 38, No. 1, pp. 345-350, Jan. 2000.

Al-Soud, W. A., et al., "Purification and Characterization of PCR-Inhibitory Components in Blood Cells," Journal of Clinical Microbiology, vol. 39, No. 2, pp. 485-493, Feb. 2001.

Altwegg, M., et al., "Amplification Methods in Diagnostic Microbiology," Journal of Microbiological Methods, vol. 23, No. 1, pp. 1-2, 1995.

Barnes, W. M., "The Fidelity of Taq Polymerase Catalyzing PCR is Improved by an N-terminal Deletion," Gene, vol. 112, pp. 29-35, 1992.

Barnes, W. M., "PCR Amplification of up to 35-kb DNA with High Fidelity and High Yield from Lamda Bacteriophage Templates," Proceedings of the National Academy of Sciences of the United States of America, vol. 91, pp. 2216-2220, 1994.

Barnes, W., "Tips and Tricks for Long and Accurate PCR," Trends in Biochemical Sciences, vol. 19, No. 8, pp. 342-343, 1994.

Baskaran, N., et al., "Uniform Amplification of a Mixture of Deoxyribonucleic Acids with Varying GC Content," Genome Research, vol. 6, No. 7, pp. 633-638, 1996.

Blatter, N., et al., "Structure and Function of an RNA-reading Thermostable DNA Polymerase," Angewandte Chemie International Edition, vol. 52, pp. 11935-11939, 2013.

Bourke, M. T., et al., "NaOH Treatment to Neutralize Inhibitors of Taq Polymerase," Journal of Forensic Sciences, vol. 44, Issue 5, pp. 1046-1050, 1999.

Burckhardt, J., "Amplification of DNA from Whole Blood," Genome Research, vol. 3, No. 4, pp. 239-243, 1994.

Cattaneo, C., et al., "Comparison of Three DNA Extraction Methods on Bone and Blood Stains up to 43 Years Old and Amplification of Three Different Gene Sequences," Journal of Forensic Sciences, vol. 42, Issue 6, pp. 1126-1135, 1997.

Chander, Y., et al., "A Novel Thermostable Polymerase for RNA and DNA Loop-mediated Isothermal Amplification (LAMP)," Frontiers in Microbiology, vol. 5, Article 395, pp. 1-11, Aug. 2014.

De Franchis, R., et al., "A Potent Inhibitor of Taq Polymerase Copurifies with Human Genomic DNA," Nucleic Acids Research, vol. 16, No. 21, p. 10355, 1988.

Dieffenbach, C. W., et al., "Setting up a PCR Laboratory," Genome Research, vol. 3, pp. S2-S7, 1993.

Dillon, C. P., et al., "RNAi as an Experimental and Therapeutic Tool to Study and Regulate Physiological and Disease Processes," Annual Review of Physiology, vol. 67, pp. 147-173, 2005.

Dykxhoorn, D. M., et al., "The Silent Revolution: RNA Interferences as Basic Biology, Research Tool, and Therapeutic," Annual Review of Medicine, vol. 56, pp. 401-423, 2005.

Elhai, J., et al., "Conjugal Transfer of DNA to Cyanobacteria," Methods in Enzymology, vol. 167, pp. 747-754, 1988.

Frackman, S., et al., "Betaine and DMSO: Enhancing Agents for PCR," Promega Notes, vol. 65, pp. 27-30, 1998.

GenBank No. AAA27507.1, "DNA Polymerase [Thermus aquaticus]," accessed from NCBI website at <http://www.ncbi.nlm.nih.gov/protein/155129?report=genbank&log$=protalign&blast_rank=>, 3 pages, Apr. 26, 1993.

GenBank Accession No. J04639, "Thermus aquaticus DNA Polymerase (Pol I) Gene," accessed from NCBI website at <http://www.ncbi.nlm.nih.gov/nuccore/155128>, 3 pages, Aug. 28, 2009.

Ghadessy, F. J., et al., "Directed Evolution of Polymerase Function by Compartmentalized Self-Replication," Proceedings of the National Academy of Sciences of the United States of America, vol. 98, No. 8, pp. 4552-4557, Apr. 2001.

Gundry, C. N., et al. "Amplicon Melting Analysis with Labeled Primers: A Closed-tube Method for Differentiating Homozygotes and Heterozygotes," Clinical Chemistry, vol. 49, No. 3, pp. 396-406, 2003.

Helene, C., et al., "Control of Gene Expression by Triple Helix-Forming Oligonucleotides. The Antigene Strategy," Annals of the New York Academy of Sciences, vol. 660, pp. 27-36, 1992.

Higuchi, R., et al., "Kinetic PCR Analysis: Real-time Monitoring of DNA Amplification Reactions," Bio/technology (Nature Publishing Company), vol. 11, No. 9, pp. 1026-1030, Sep. 1993.

Ignatov, K. B., et al., "Substitution of Asn for Ser543 in the Large Fragment of Taq DNA Polymerase Increases the Efficiency of Synthesis of Long DNA Molecules," FEBS Letters, vol. 425, pp. 249-250, 1998.

International Search Report issued for PCT/US2016/032041, dated Aug. 31, 2016, 4 pages, 2016.

Izraeli, S., et al., "Detection of Gene Expression by PCR Amplification of RNA Derived from Frozen Heparinized Whole Blood," Nucleic Acids Research, vol. 19, No. 21, p. 6051, 1991.

(56) References Cited

OTHER PUBLICATIONS

Kellogg, D. E., et al., "TaqStart Antibody (TM): "Hot Start" PCR Facilitated by a Neutralizing Monoclonal Antibody Directed Against Taq DNA Polymerase," BioTechniques, vol. 16, No. 6, pp. 1134-1137, 1994.

Kermekchiev, M. B., et al., "Cold-sensitive Mutants of Taq DNA Polymerase Provide a Hot Start for PCR," Nucleic Acids Research, vol. 31, No. 21, pp. 6139-6147, 2003.

Kermekchiev, M. B., et al., "Mutants of Taq DNA Polymerase Resistant to PCR Inhibitors Allow DNA Amplification From Whole Blood and Crude Soil Samples," Nucleic Acids Research, vol. 37, No. 5, e40, pp. 1-14, 2009.

Klein, A., et al., "Comparison of Methods for Extraction of Nucleic Acid from Hemolytic Serum for PCR Amplification of Hepatitis B Virus DNA Sequences," Journal of Clinical Microbiology, vol. 35, No. 7, pp. 1897-1899, Jul. 1997.

Kox, L. F. F., et al., "A More Reliable PCR for Detection of *Mycobacterium tuberculosis* in Clinical Samples," Journal of Clinical Microbiology, vol. 32, No. 3, pp. 672-678, Mar. 1994.

Kramvis, A., et al., "Comparison of Hepatitis B Virus DNA Extractions from Serum by the QIAamp Blood Kit, GeneReleaser, and the Phenol-Chloroform Method," Journal of Clinical Microbiology, vol. 34, No. 11, pp. 2731-2733, Nov. 1996.

Lamontagne, M. G., et al., "Evaluation of Extraction and Purification Methods for Obtaining PCR-amplifiable DNA from Compost for Microbial Community Analysis," Journal of Microbiological Methods, vol. 49, pp. 255-264, 2002.

Lantz, P.-G., et al., "Biotechnical Use of Polymerase Chain Reaction for Microbiological Analysis of Biological Samples," Biotechnology Annual Review, vol. 5, pp. 87-130, 2000.

Lawyer, F. C., et al., "Isolation, Characterization, and Expression in *Escherichia coli* of the DNA Polymerase Gene from Thermus aquaticus," Journal of Biological Chemistry, vol. 264, No. 11, pp. 6427-6437, 1989.

Lee, J. F., et al., "Aptamer Therapeutics Advance," Current Opinion in Chemical Biology, vol. 10, pp. 282-289, 2006.

Li, Y., et al., "Crystal Structures of Open and Closed Forms of Binary and Ternary Complexes of the Large Fragment of Thermus aquaticus DNA Polymerase I: Structural Basis for Nucleotide Incorporation," The EMBO Journal, vol. 17, No. 24, pp. 7514-7525, 1998.

Link, A. J., et al., "Beyond Toothpicks: New Methods for Isolating Mutant Bacteria," Nature Reviews, vol. 5, pp. 680-688, 2007.

Livingstone, C. D., et al., "Protein Sequence Alignments: A Strategy for the Hierarchical Analysis of Residue Conservation," Computer Applications in the Biosciences: CABIOS, vol. 9, No. 6, pp. 745-756, 1993.

Maher, III, L. J., "DNA Triple-Helix Formation: An Approach to Artificial Gene Repressors?," BioEssays, vol. 14, No. 12, pp. 807-815, Dec. 1992.

Martin, B. R., et al., "Mammalian Cell-based Optimization of the Biarsenical-binding Tetracysteine Motif for Improved Fluorescence and Affinity," Nature Biotechnology, vol. 23, pp. 1308-1314, 2005.

Monis, P. T., et al., "Comparison of SYT09 and SYBR Green I for Real-time Polymerase Chain Reaction and Investigation of the Effect of Dye Concentration on Amplification and DNA Melting Curve Analysis," Analytical Biochemistry, vol. 340, pp. 24-34, 2005.

Morata, P., et al., "Strategy for Optimizing DNA Amplification in a Peripheral Blood PCR Assay Used for Diagnosis of Human Brucellosis," Journal of Clinical Microbiology, vol. 36, No. 9, pp. 2443-2446, Sep. 1998.

Myers, T. W., et al., "Reverse Transcription and DNA Amplification by a Thermus thermophilus DNA Polymerase," Biochemistry, vol. 30, No. 31, pp. 7661-7666, 1991.

Nath, K., et al., "Effects of Ethidium Bromide and SYBR(R) Green I on Different Polymerase Chain Reaction Systems," Journal of Biochemical and Biophysical Methods, vol. 42, pp. 15-29, 2000.

Ngo, J. T., et al., "Computational Complexity, Protein Structure Prediction, and the Levinthal Paradox," The Protein Folding Problem and Tertiary Structure Prediction, pp. 491-495, 1994.

Ong, J. L., et al., "Directed Evolution of DNA Polymerase, RNA Polymerase and Reverse Transcriptase Activity in a Single Polypeptide," Journal of Molecular Biology, vol. 361, No. 3, pp. 537-550, 2006.

Panaccio, M., et al., "PCR Based Diagnosis in the Presence of 8% (v/v) Blood," Nucleic Acids Research, vol. 19, No. 5, p. 1151, 1991.

Pushparaj, P. N., et al., "Short Interfering RNA (siRNA) as a Novel Therapeutic," Clinical and Experimental Pharmacology and Physiology, vol. 33, pp. 504-510, 2006.

Reynolds, A., et al., "Rational siRNA Design for RNA Interference," Nature Biotechnology, vol. 22, No. 3, pp. 326-330, Mar. 2004.

Rossen, L., et al., "Inhibition of PCR by Components of Food Samples, Microbial Diagnostic Assays and DNA-extraction Solutions," International Journal of Food Microbiology, vol. 17, pp. 37-45, 1992.

Sagner, G., et al., "Rapid Filter Assay for the Detection of DNA Polymerase Activity: Direct Identification of the Gene for the DNA Polymerase from Thermus aquaticus," Gene, vol. 97, pp. 119-123, 1991.

Scalice, E. R., et al., "Monoclonal Antibodies Prepared Against the DNA Polymerase from Thermus aquaticus are Potent Inhibitors of Enzyme Activity," Journal of Immunological Methods, vol. 172, pp. 147-163, 1994.

Sharkey, D. J., et al., "Antibodies as Thermolabile Switches: High Temperature Triggering for the Polymerase Chain Reaction," Bio/technology, vol. 12, pp. 506-509, 1994.

Steitz, T. A., "DNA Polymerases: Structural Diversity and Common Mechanisms," The Journal of Biological Chemistry, vol. 274, No. 25, pp. 17395-17398, Jun. 1999.

Stubner, S., "Enumeration of 16S rDNA of Desulfotomaculum Lineage 1 in Rice Field Soil by Real-time PCR with SybrGreen (TM) Detection," Journal of Microbiological Methods, vol. 50, pp. 155-164, 2002.

Studier, F. W., "Protein Production by Auto-Induction in High-Density Shaking Cultures," Protein Expression and Purification, vol. 41, pp. 207-234, 2005.

Tabor, S., et al., "A Single Residue in DNA Polymerase of the *Escherichia coli* DNA Polymerase I Family is Critical for Distinguishing Between Deoxy- and Dideoxyribonucleotides," Proceedings of the National Academy of Sciences of the United States of America, vol. 92, pp. 6339-6343, Jul. 1995.

Tawfik, D. S., et al., "Man-made Cell-like Compartments for Molecular Evolution," Nature Biotechnology, vol. 16, pp. 652-656, 1998.

Tomita, N., et al., "Loop-mediated Isothermal Amplification (LAMP) of Gene Sequences and Simple Visual Detection of Products," Nature Protocols, vol. 3, No. 5, pp. 877-882, 2008.

Topal, M. D., et al., "Products of Bacteriophage T4 Genes 32 and 45 Improve the Accuracy of DNA Replication in Vitro," The Journal of Biological Chemistry, vol. 258, No. 20, pp. 12274-12279, 1983.

Tsai, Y.-L., et al., "Rapid Method for Separation of Bacterial DNA from Humic Substances in Sediments for Polymerase Chain Reaction," Applied and Environmental Microbiology, vol. 58, No. 7, pp. 2292-2295, Jul. 1992.

United States Patent and Trademark Office in connection with U.S. Appl. No. 14/055,796, filed Oct. 16, 2013, "Restriction Requirement", 10 pages, mailed Mar. 12, 2015.

United States Patent and Trademark Office in connection with U.S. Appl. No. 14/055,796, filed Oct. 16, 2013, "Response to Restriction and Election Requirements", 4 pages, dated Jun. 11, 2015.

United States Patent and Trademark Office in connection with U.S. Appl. No. 14/055,796, filed Oct. 16, 2013, "Non-Final Office Action", 13 pages, mailed Jul. 7, 2015.

United States Patent and Trademark Office in connection with U.S. Appl. No. 14/055,796, filed Oct. 16, 2013, "Amendment and Response to Office Action", 15 pages, dated Oct. 30, 2015.

United States Patent and Trademark Office in connection with U.S. Appl. No. 14/055,796, filed Oct. 16, 2013, "Non-Final Office Action", 27 pages, mailed Dec. 17, 2015.

(56) References Cited

OTHER PUBLICATIONS

United States Patent and Trademark Office in connection with U.S. Appl. No. 14/055,796, filed Oct. 16, 2013, "Amendment and Response to Office Action", 12 pages, dated Jan. 19, 2016.

United States Patent and Trademark Office in connection with U.S. Appl. No. 14/055,796, filed Oct. 16, 2013, "Final Office Action", 32 pages, mailed Apr. 20, 2016.

United States Patent and Trademark Office in connection with U.S. Appl. No. 14/055,796, filed Oct. 16, 2013, "Interview Summary and Amendment and Response to Final Office Action Under 37 C.F.R. § 1.116", 30 pages, dated Aug. 18, 2016.

United States Patent and Trademark Office in connection with U.S. Appl. No. 14/055,796, filed Oct. 16, 2013, "Non-Final Office Action", 27 pages, mailed Dec. 12, 2016.

United States Patent and Trademark Office in connection with U.S. Appl. No. 14/055,796, filed Oct. 16, 2013, "Amendment & Response to Office Action Dated Dec. 12, 2016", 16 pages, dated Jun. 9, 2017.

United States Patent and Trademark Office in connection with U.S. Appl. No. 14/055,796, filed Oct. 16, 2013, "Final Office Action", 21 pages, Notification date Jul. 5, 2017.

United States Patent and Trademark Office in connection with U.S. Appl. No. 14/055,796, filed Oct. 16, 2013, "Amendment & Response to Final Office Action dated Jul. 5, 2017", 104 pages, dated Jul. 5, 2017.

Watson, R. J., et al., "Purification and Characterization of a Common Soil Component Which Inhibits the Polymerase Chain Reaction," Canadian Journal of Microbiology, vol. 46, pp. 633-642, 2000.

Wilson, I. G. "Inhibition and Facilitation of Nucleic Acid Amplification," Applied and Environmental Microbiology, vol. 63, No. 10, pp. 3741-3751, Oct. 1997.

International Searching Authority in connection with PCT/US2016/032041, "Written Opinion of the International Searching Authority", 5 pages, mailed Aug. 31, 2016.

Yamagami, T., et al., "Mutant Taq DNA Polymerases with Improved Elongation Ability as a Useful Reagent for Genetic Engineering," Frontiers in Microbiology, vol. 5, Article 461, pp. 1-10, Sep. 2014.

Yeates, C., et al., "Methods for Microbial DNA Extraction from Soil for PCR Amplification," Biological Procedures Online, vol. 1, No. 1, pp. 40-47, 1998.

Zhang, Z., et al., "Direct DNA Amplification from Crude Clinical Samples Using a PCR Enhancer Cocktail and Novel Mutants of Taq," Journal of Molecular Diagnostics, vol. 12, No. 2, pp. 152-161, Mar. 2010.

Zhong, X. Y., et al., "Sensitive and Specific Detection of Carcinoembryonic Antigen cDNA Using the Hot Start Polymerase Chain Reaction Technique," Clinical Laboratory Publications, vol. 46, pp. 7-11, 2000.

Ederth, J., et al., "Functional Interplay Between the Jaw Domain of Bacterial RNA Polymerase and Allele-Specific Residues in the Product RNA-Binding Pocket," Journal of Molecular Biology, vol. 356, No. 5, pp. 1163-1179, 2006.

Ignatov, et al., Biotechniques, vol. 57, No. 2, pp. 81-87, Aug. 2014.

Lambda DNA
3 hours
(not optimized, 4 primers)

Published mutations for RT activity for Klentaq

S515R  I638F  M747K  L459M

RT-KTq2   white 50 mM Tris-HCl (pH 9.2), 16 mM (NH4)2SO4, 0.1 % Tween 20, 7.5 mM MgCl2, 500 ħM of each dNTP, 0.8 M betaine, 600 nM of each primer, 100 nM of the respective TaqMan probe. 5:1::RT-KTq2:Taq Nina Blatter, Konrad Bergen, Oliver Nolte, Wolfram Welte, Kay Diederichs, Jutta Mayer, Markus Wieland, and Andreas Marx (2013) Angewandte Chemie International Edition 52:11935-11939

E602V A608V IE614MG Taq
(rNTP also)

green

Ong, Jennifer L Loakes, David Jaroslawski, Szymon Too, Kathleen Holliger, Philipp (2006) JMB

FIG. 10

MUTANT POLYMERASES AND USES THEREOF

CROSS-REFERENCE TO RELATED APPLICATIONS

The present application is a continuation of U.S. patent application Ser. No. 17/303,445, filed May 28, 2021, which is a continuation of U.S. patent application Ser. No. 15/572,693, filed Nov. 8, 2017, which is the U.S. National Stage Application of PCT Application No. PCT/US2016/032041, filed May 12, 2016, which claims the benefit of U.S. Provisional Application Ser. No. 62/160,404, filed May 12, 2015. Each of the above-cited applications is incorporated herein by reference in its entirety.

STATEMENT REGARDING FEDERALLY SPONSORED RESEARCH OR DEVELOPMENT

This invention was made with government support under grant number 1R21HG006291 awarded by National Institutes of Health; 2R44GM088948 awarded by National Institutes of Health; and IIP-1127479 awarded by National Science Foundation. The government has certain rights in the invention.

MATERIAL INCORPORATED-BY-REFERENCE

The contents of the XML file submitted electronically herewith are incorporated herein by reference in their entirety: A computer readable format copy of the Sequence Listing (filename: P13550US03.xml, date created: Sep. 26, 2023, file size 43,907 bytes).

BACKGROUND OF THE INVENTION

Despite a close similarity of two well-known thermotolerant DNA polymerases (Taq large fragment, known as Klentaq1 (SEQ ID NO: 2), and Bst large fragment, e.g., SEQ ID NO: 10) as to their crystal structures and 50% sequence identity, only Taq (SEQ ID NO: 1) and Klentaq1 (SEQ ID NO: 2) DNA polymerase can catalyze PCR (during which enzyme must repeatedly withstand 94° C.) but the analogous Bst DNA polymerase denatures at 65-70° C. and therefore cannot catalyze PCR. Klentaq1 (SEQ ID NO: 1) cannot copy double-stranded DNA by displacing a DNA strand ahead of it, and the 5'-(flap) endonuclease of Taq (SEQ ID NO: 1) degrades displaced DNA; but Bst can efficiently strand-displace without degradation, and hence is conventionally used to catalyze loop-mediated isothermal amplification (LAMP), which requires double-strand invasion and efficient strand-displacement. None of these enzymes (e.g., Taq, Klentaq, Bst) are known for reverse transcriptase (RT) activity, so conventionally a separate RT enzyme is combined with them to accomplish RT-PCR (reverse transcriptase polymerase chain reaction) or likewise RT-LAMP.

The mechanism of DNA polymerases of family A can be anthropomorphically understood as fingers and thumb, opening and closing, since they resemble a right hand. The crystal structure of Klentaq1 (SEQ ID NO: 2) with primer/template DNA has been shown to demonstrate both open and closed forms in the same crystal (Li et al. 1998 The EMBO Journal 17, 7514-7525). Dozens of crystal structures of each of these enzymes have not yet explained why Klentaq1 enzyme cannot perform the functions exhibited by other DNA polymerases, such as copying RNA into DNA (i.e., reverse transcriptase activity) or copying double-stranded DNA (displacing the non-template strand, or strand displacement activity), which can be catalyzed by the homologous large fragment of Bst DNA polymerase (e.g., SEQ ID NO: 10 or Bst 2.0, New England Biolabs), used for the isothermal method LAMP (Tomita et al. 2008 Nature Protocols 3, 877-882). Also unexplained are the mechanisms of (mostly unknown) inhibitor chemicals that can prevent successful PCR analysis of blood, urine or food-safety cultures. Food safety assays, often even after pathogen enrichment culture and partial DNA purification, are unreliable due to inhibitors, particularly for chocolate and black pepper. Food safety analysis can be limited for PCR and RT-PCR by enzyme inhibitors, particularly chocolate and pepper. As such, food or food-bacteria enriched culture RNA or DNA may require purification before PCR analysis, with varying success, convenience, and expense.

Although full-length, wild-type Taq (SEQ ID NO: 1) can strand-displace to some extent, its 5'-endonuclease (flap endonuclease, FEN), according to previous studies using only enzymes without this domain, cleaves the displaced strand so much that it is not appropriate for LAMP. Two studies have selected different combinations of four amino acid changes that demonstrate reverse transcriptase activity for Klentaq1 (Blatter et al. 2013 Angewandte Chemie International Edition 52, 11935-11939) or Taq DNA polymerase (Ong et al. 2006 Journal of Molecular Biology 361, 537-550).

Known mutant polymerases include Omni Taq, i.e., FL-22 (as described in U.S. Patent Application Publication No. 2011/0027832) and Omni Klentaq, i.e., KlenTaq-10 (as described in U.S. Patent Application Publication No. 2006/0084074). Known mutant polymerases and uses thereof are described in, for example, U.S. Pat. No. 7,462,475, issued 9 Dec. 2008; U.S. Patent Application Publication No. 2009/0170060, published 2 Jul. 2009; U.S. Patent Application Publication No. 2011/0027832, published 3 Feb. 2011; U.S. Patent Application Publication No. 2012/0028259, published 2 Feb. 2012; international PCT application WO2012/088479, published 28 Jun. 2012; U.S. Patent Application Publication No. 2014/0113299, published 24 Apr. 2014.

SUMMARY OF THE INVENTION

Among the various aspects of the present disclosure is the provision of mutant polymerases having DNA polymerase activity and reverse transcriptase activity or strand displacement activity.

Another aspect provides for methods of amplifying a target nucleic acid using mutant polymerases having DNA polymerase activity and reverse transcriptase activity or strand displacement activity.

In some embodiments of the methods, amplifying comprises reverse transcriptase PCR (RT-PCR). In some embodiments, amplifying comprises loop-mediated isothermal amplification (LAMP). In some embodiments, LAMP is performed with a hanging drop hot start. In some embodiments, amplifying comprises reverse transcriptase loop-mediated isothermal amplification (RT-LAMP). In some embodiments, RT-LAMP is performed with a hanging drop hot start.

In some embodiments of the methods, the mutant polymerase includes a polypeptide having (a) at least 95% sequence identity to SEQ ID NO: 1 or SEQ ID NO: 2, (b) DNA polymerase activity and reverse transcriptase activity and/or strand displacement activity, (c) at least one substitution selected from the group consisting of D732N and the combination of E742R and A743R (EA742RR) (per wild type Taq numbering), and (iv) optionally, a F1AsH insertion, such as FLNCCPGCC between position 738 and position 739 (per wild type Taq numbering). In some embodiments, the mutant polymerase further includes at least one mutation selected from the group consisting of L609P, E626K, V649I, I707L, E708K, E708L, E708N, E708Q, E708I, E708W, E708R, E708V, E708S, E404G, G418E, V453L, A454S, R487G, I528M, L533R, D551G, D578E, I599V, L657Q, K738R, L781 I, and E818V (per wild-type Taq numbering), or any combination thereof. In other embodiments, the mutant polymerase further includes at least one mutation selected from the group consisting of D119A, D119N, E742R and A743R (per wild-type Taq numbering), or any combination thereof.

In some embodiments of the methods, the amplifying comprises an assay mixture including (A) a sample comprising a target RNA, (B) primers specific for the target RNA or cDNA transcribed from the target RNA, (C) a buffer, and (D) at least one mutant polymerase comprising a polypeptide sequence having (i) at least 95% sequence identity to SEQ ID NO: 1 or SEQ ID NO: 2, (ii) reverse transcriptase activity and DNA polymerase activity, and (iii) at least one substitution selected from the group consisting of D732N and the combination of E742R and A743R (EA742RR) (per wild type Taq numbering); and amplifying the target nucleic acid in the assay mixture in RT-PCR.

In some embodiments of the methods, the assay mixture does not include a separate reverse transcription enzyme or $Mn^{++}$ ion.

In some embodiments of the methods, the assay mixture includes a sample including a target RNA not purified prior to addition to the assay mixture.

In some embodiments of the methods, the assay mixture includes an inhibitory substance in an amount sufficient to cause a wild type Taq polymerase to fail to amplify the target nucleic acid in the RT-PCR. In certain embodiments of the methods, the inhibitory substance includes whole blood, a blood traction, chocolate, peanut butter, milk, seafood, meat, egg, or a soil extract.

In some embodiments of the methods, the PCR is a real-time PCR; the assay mixture further comprises at least one dye; and amplifying the target nucleic acid comprises amplifying the target nucleic acid in the assay mixture in a real-time PCR.

In some embodiments of the methods, the mutant polymerase includes at least one mutant polymerase including a F1AsH insertion of FLNCCPGCC between position 738 and position 739 (per wild type Taq numbering).

Another aspect provides for a kit for use of methods of amplifying a target nucleic acid using mutant polymerases having DNA polymerase activity and reverse transcriptase activity or strand displacement activity.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

Figure 4:
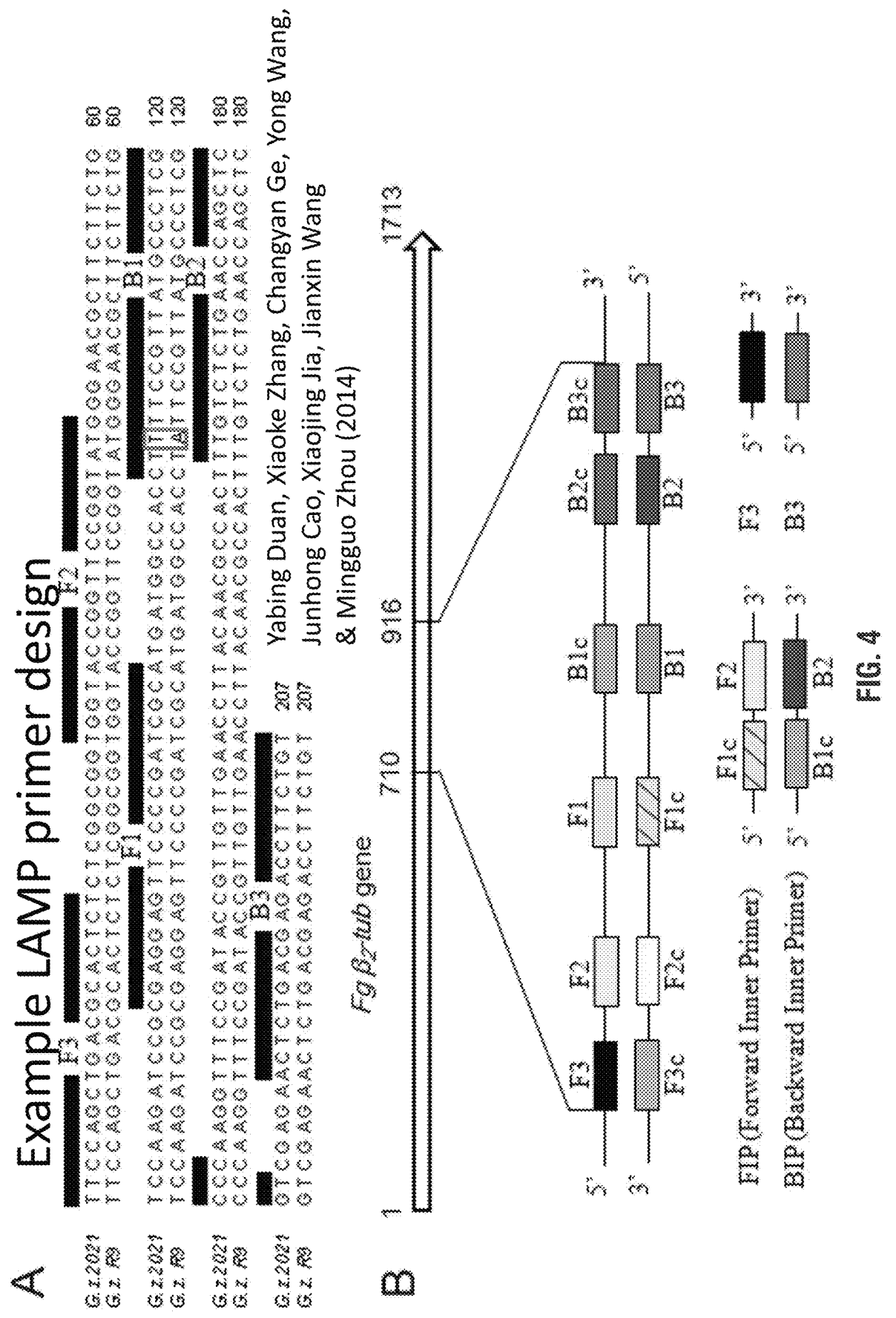

FIG. 4 is a diagram illustrating loop-mediated isothermal amplification (LAMP). In short, LAMP primers (e.g., from a set of six) "FiP" and "BiP" (or rather their complements after they are copied) hook back on themselves and prime synthesis the other way, at isothermal temperatures of about 60-70° C. LAMP is further described herein.

FIG. 6 also shows a cartoon of the 1.2 kb loop structure and the 2.4 kb displaced strand. This assay was designed so that strand-displacement would cause a band at 2.4 kb, rather than a smear with other assays. Mutant A111, i.e., TaqD732N (SEQ ID NO: 3) did surprisingly well in this assay.

Figure 8:
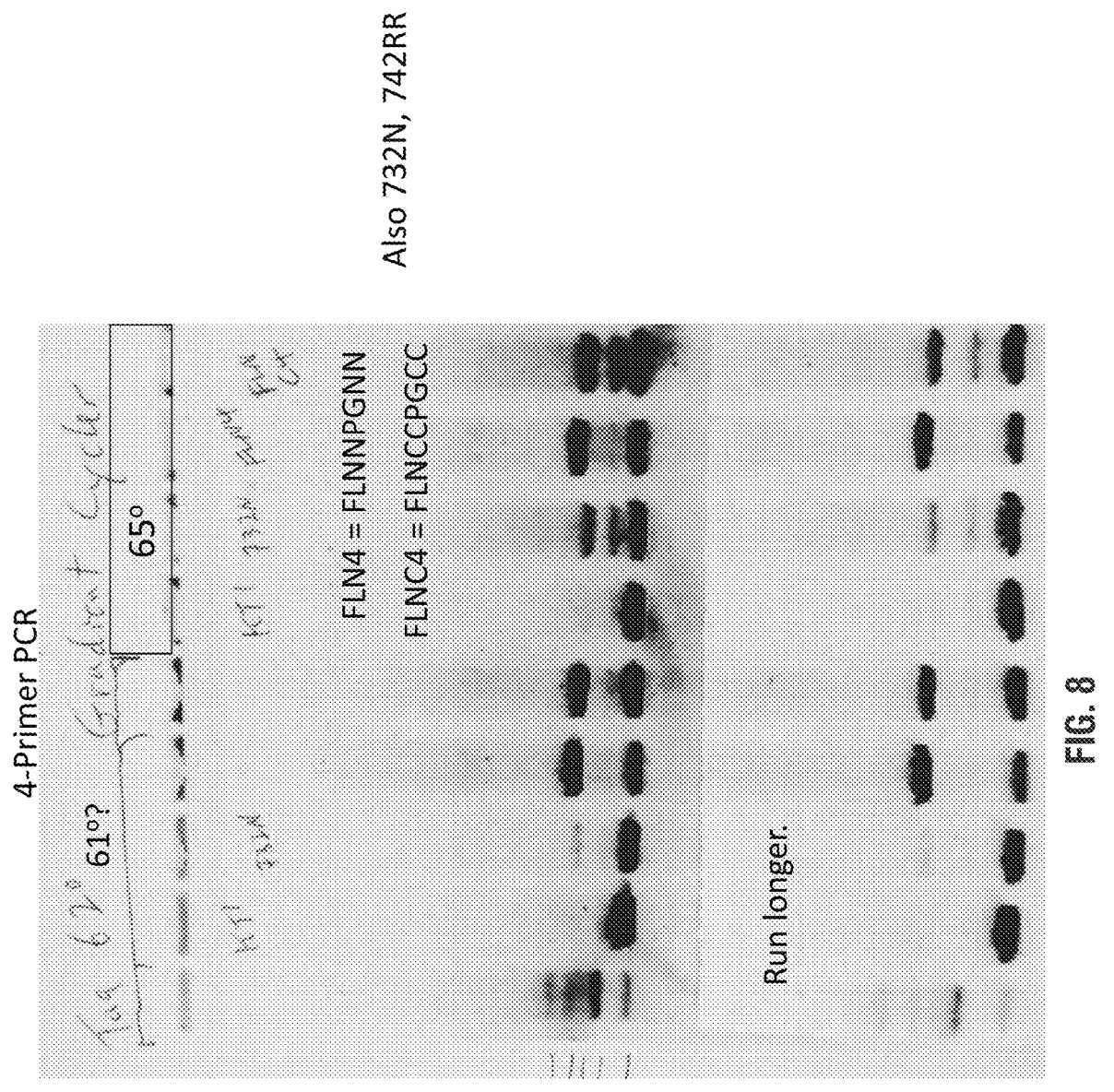

FIG. 8 is a gel image showing a four-primer PCR test. Wild-type Taq (lane 1) actually can make all four expected products. FIG. 8 shows that when the F1AsH-binding sequence was inserted between positions 738 and 739, and the polymerase also contained the D732N, E742R, and A743R mutations, differences in strand displacement efficiency were observed depending on the temperature of the PCR extension step. Conventional LAMP protocols are reported to need optimizing for temperature in this zone.

FIG. 9 shows a 4 primer (non-optimized assay) for strand displacement activity run at 60° C. and 70° C. Control was Manta polymerase (a Bst DNA large fragment polymerase).

Mutant polymerase KTflnC4RR (truncated polymerase having D732N; FLNCCPGCC insert at 738,739; and E742R and A743R (EA742RR); SEQ ID NO: 9) showed strand displacement activity, notably at 70° C. where Manta was inactivated. It was observed that LAMP was catalyzed by a Taq or Klentaq mutant enzyme, compared to Bst DNA polymerase Manta (supplied by Enzymatics).

FIG. 10 is a diagram showing known mutations for RT activity in Taq and Klentaq (Blatter et al. 2013 Angewandte Chemie International Edition 52, 11935-11939) or Taq DNA polymerase (Ong et al. 2006 Journal of Molecular Biology 361, 537-550). When the four known mutations of Blatter et al. (S515R, I638F, M747K, L459M per wild-type Taq numbering) were added to Klentaq1 having D732N, no PCR activity was observed.

Figure 11:
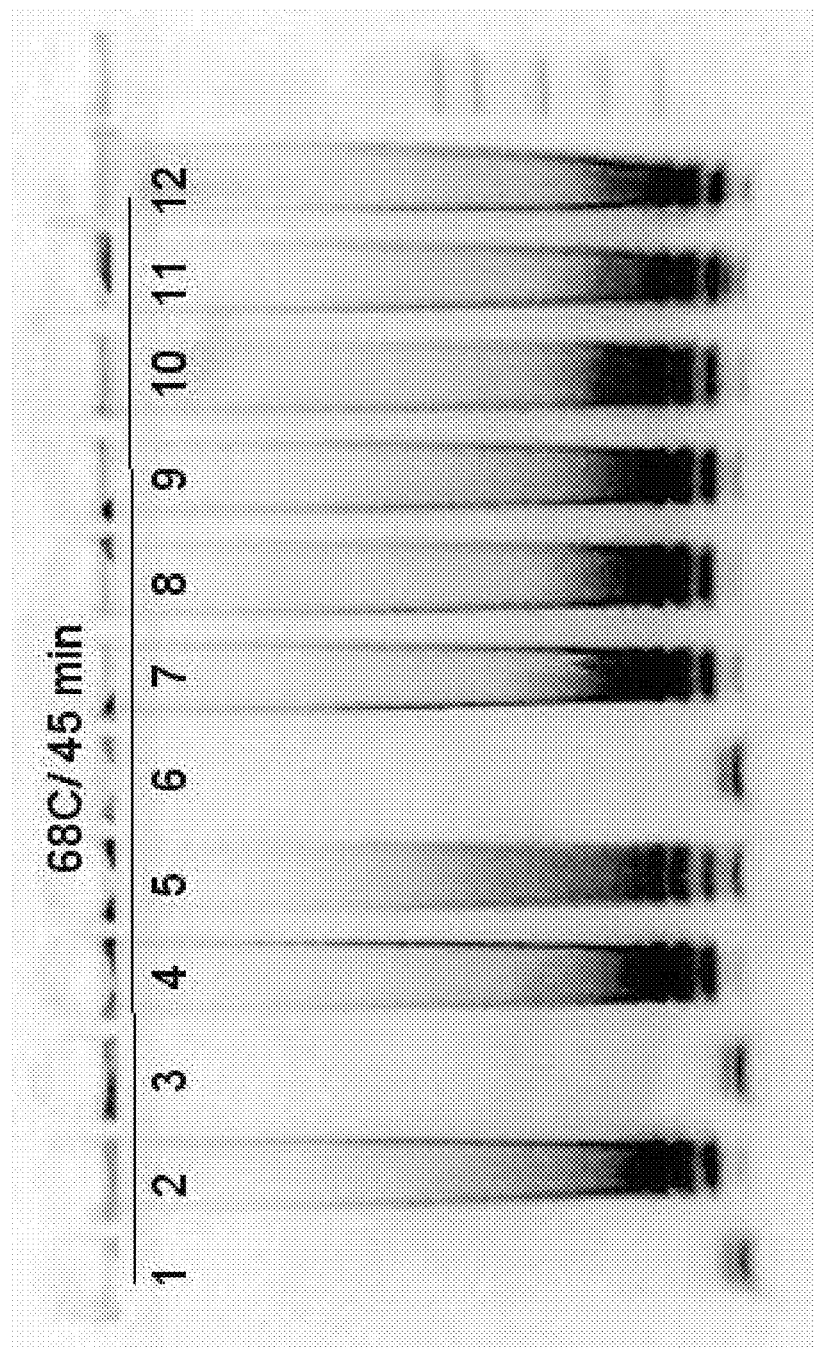

FIG. 11 is an image of a LAMP assay using the 6-primer LAMP set published by Lucigen for RT-LAMP of MS2 RNA. Surprisingly and unexpectedly, Klentaq D732N (SEQ ID NO: 4) worked from the RNA template (see lane 2). In the 45 minute assay, mutants having both E742R and A743R substitutions (EA742RR) and F1AsH inserts at 738,739 had improved performance over other enzymes.

Figure 12:
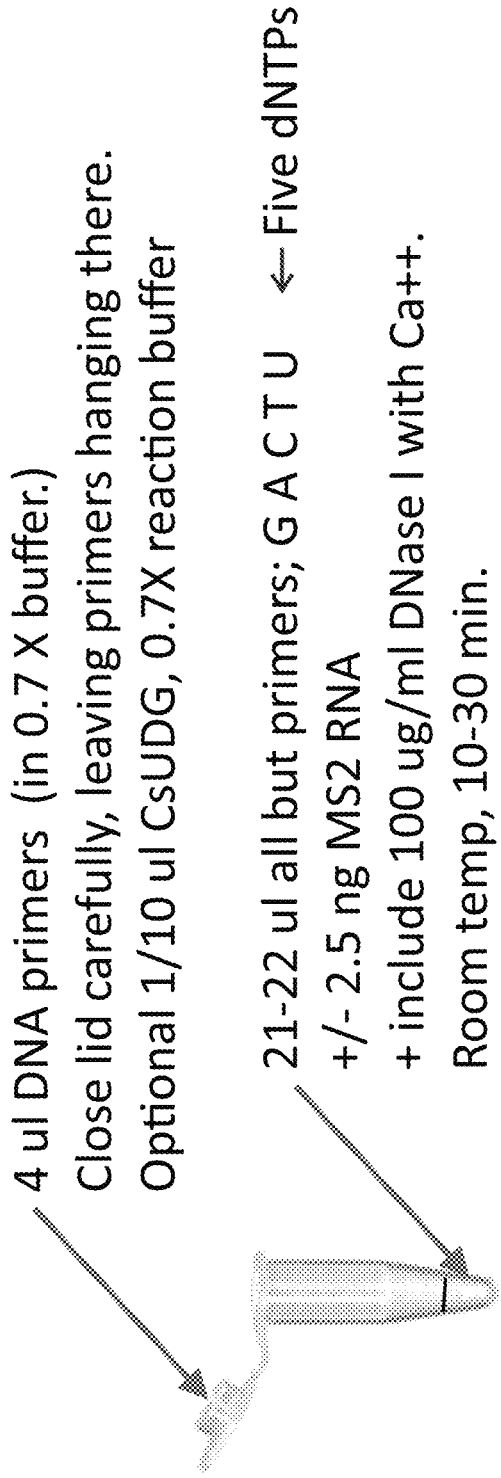

FIG. 12 is a diagram depicting hanging drop hot start for RT-PCR or RT-LAMP. No-template amplification can be caused by PCR or LAMP product contamination in an environment. DNAse I and off cite preparation of primers can at least in part address such contamination. The hanging drop hot start protocol can also be used to get RNA-dependent amplification. RNase I reduces or eliminates the RNA-amplified product (data not shown) if the RNAse I digest is done in 1/10 strength buffer.

Figure 13:
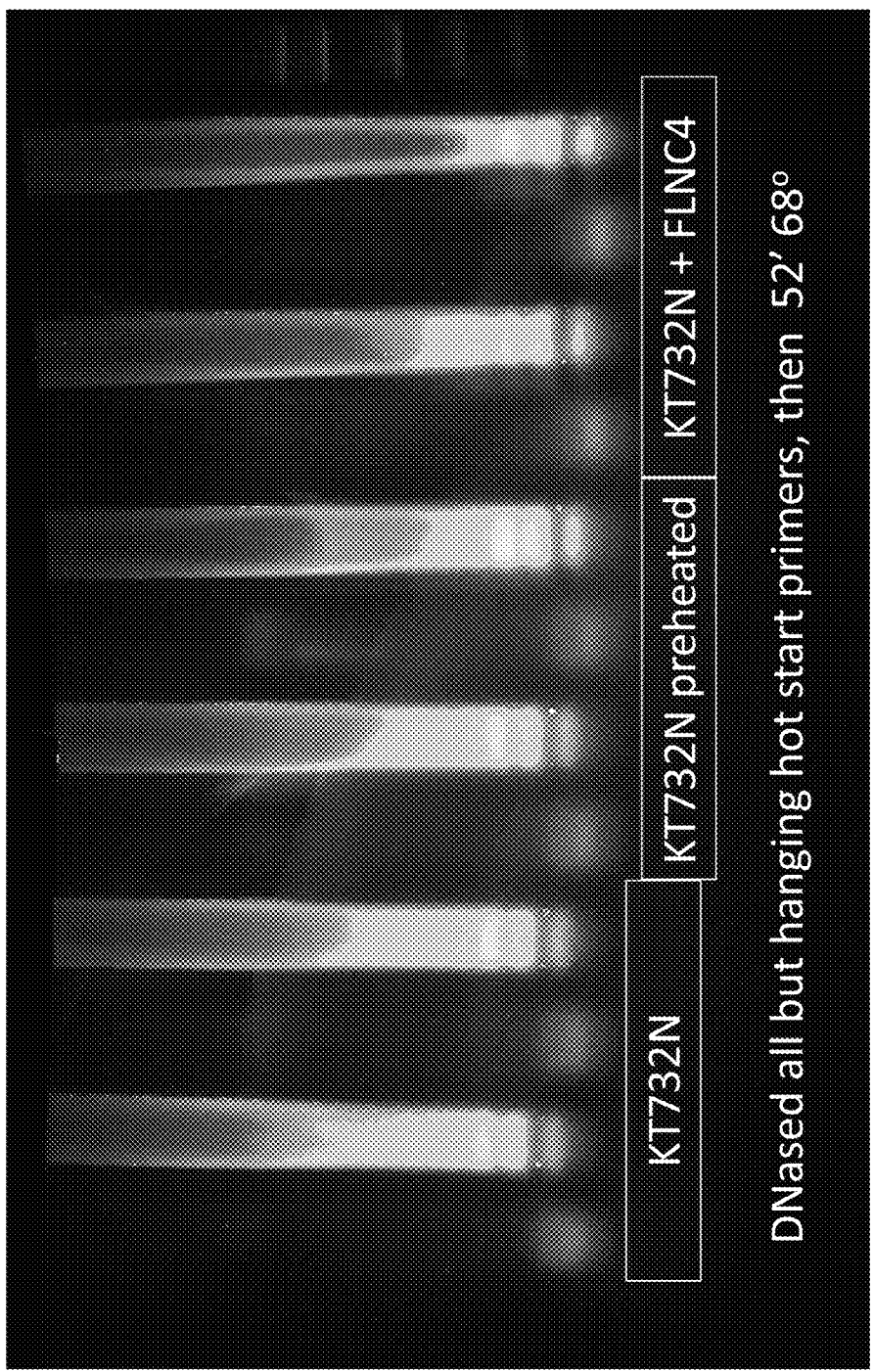

FIG. 13 shows an image from a LAMP reaction monitored via real-time fluorescence change (using Eva Green dye) for FT732N (SEQ ID NO: 4), FT732N (SEQ ID NO: 4) preheated, and KT732-FLNCY-E742R-A743R (KT732-FLNCY-EA742RR; SEQ ID NO: 9).

Figure 14A:
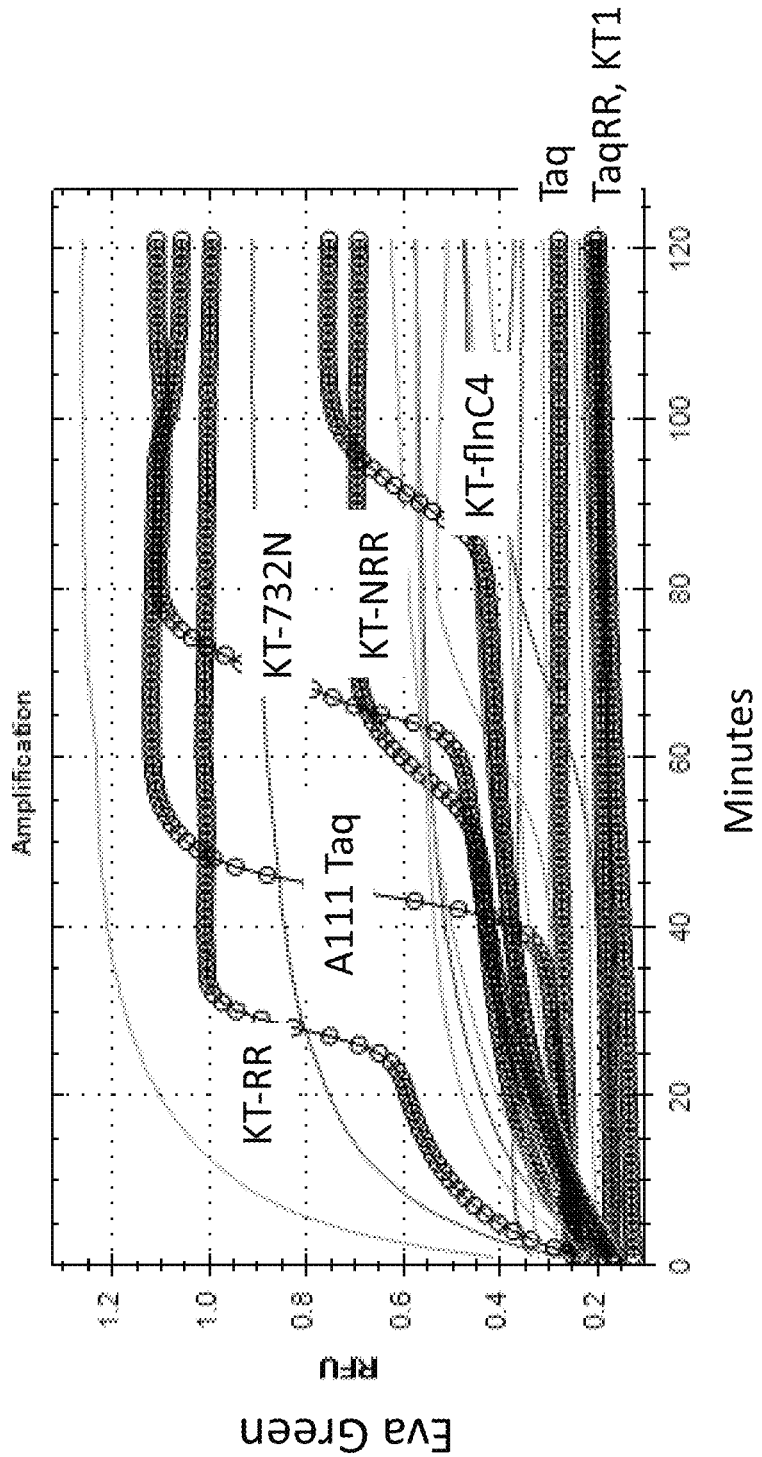
Figure 14B:
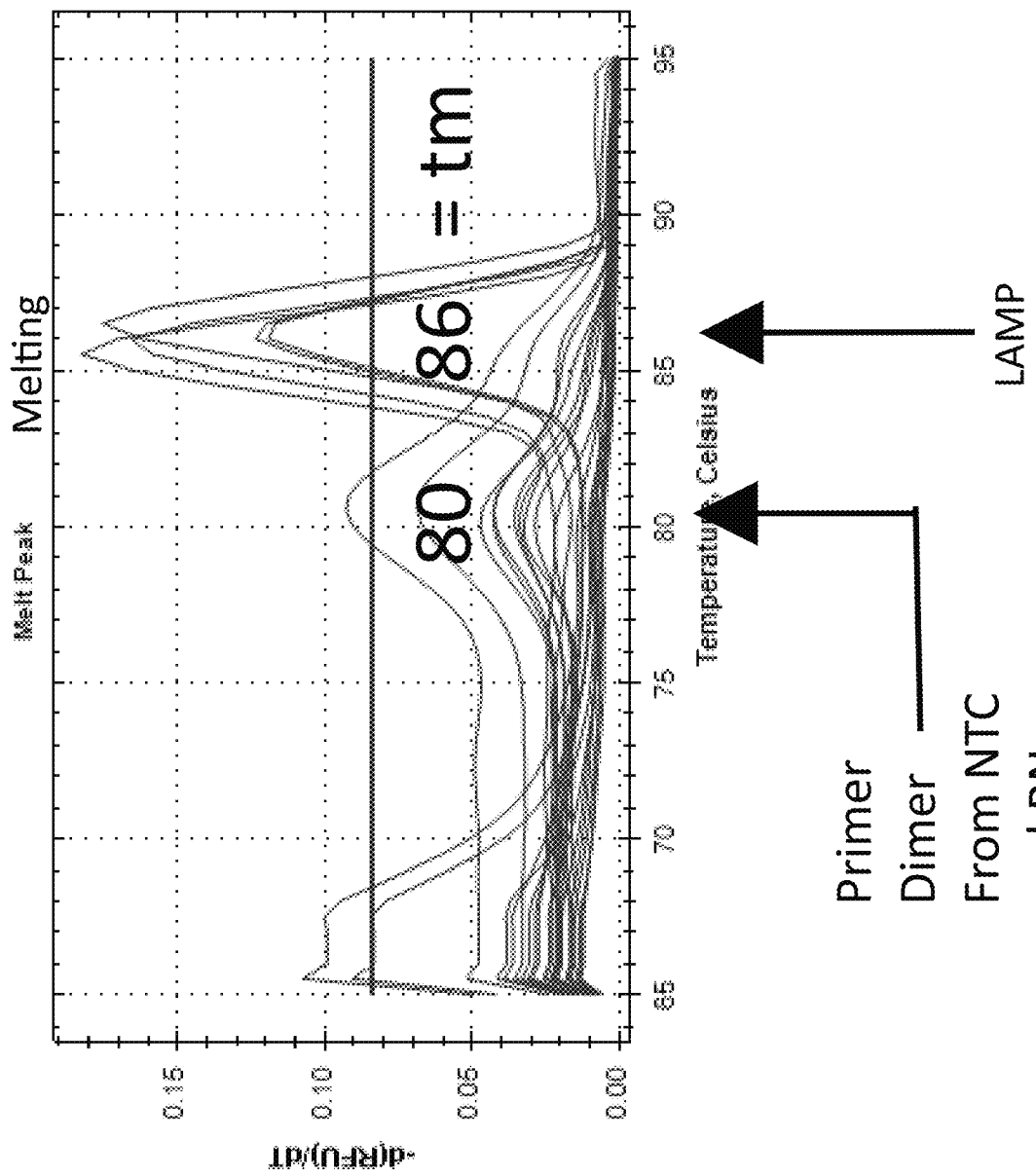

FIG. 14A shows RT-LAMP real-time traces with no RT enzyme and no $Mn^{+/+}$ using Eva Green indicator for tested mutant polymerases (KT-RR, SEQ ID NO: 6; Taq-D732N, SEQ ID NO: 3; KT-732, SEQ ID NO: 4; KT-NRR, SEQ ID NO: 8; and KT-flnC4, SEQ ID NO: 9; Taq, SEQ ID NO: 1; TaqRR, SEQ ID NO: 5; and Klentaq1, SEQ ID NO: 2). Buffer conditions are 50 mM Tris-HCl, pH 8.55, 8 mM ammonium sulfate, 200 µM each dNTP, 0.75 M betaine, 0.025% Brij58. On the trace diagrams, inflected curves indicate positive LAMP reactions. FIG. 14B shows melting curves, where genuine LAMP products melted at 85-86.5° C. After eliminating inserts at 738,739 and the D732N, a Klentaq1 polymerase with only E742R and A743R (EA742RR) (SEQ ID NO: 6) had the best performance of the enzymes tested. Mutant polymerase A111 (having D732N, SEQ ID NO: 3) had surprisingly good performance (despite having a 5'-flap endonuclease that should theoretically be preventing any LAMP) with a good curve (much lower background of "primer-dimer" synthesis). Taq with E742R and A743R (EA742RR) (SEQ ID NO: 5) and Taq (SEQ ID NO: 1) did not work in the assay shown in FIG. 14. On a gel, the Taq products look different, which may be some 5'-exonuclease activity showing.

Figure 15:
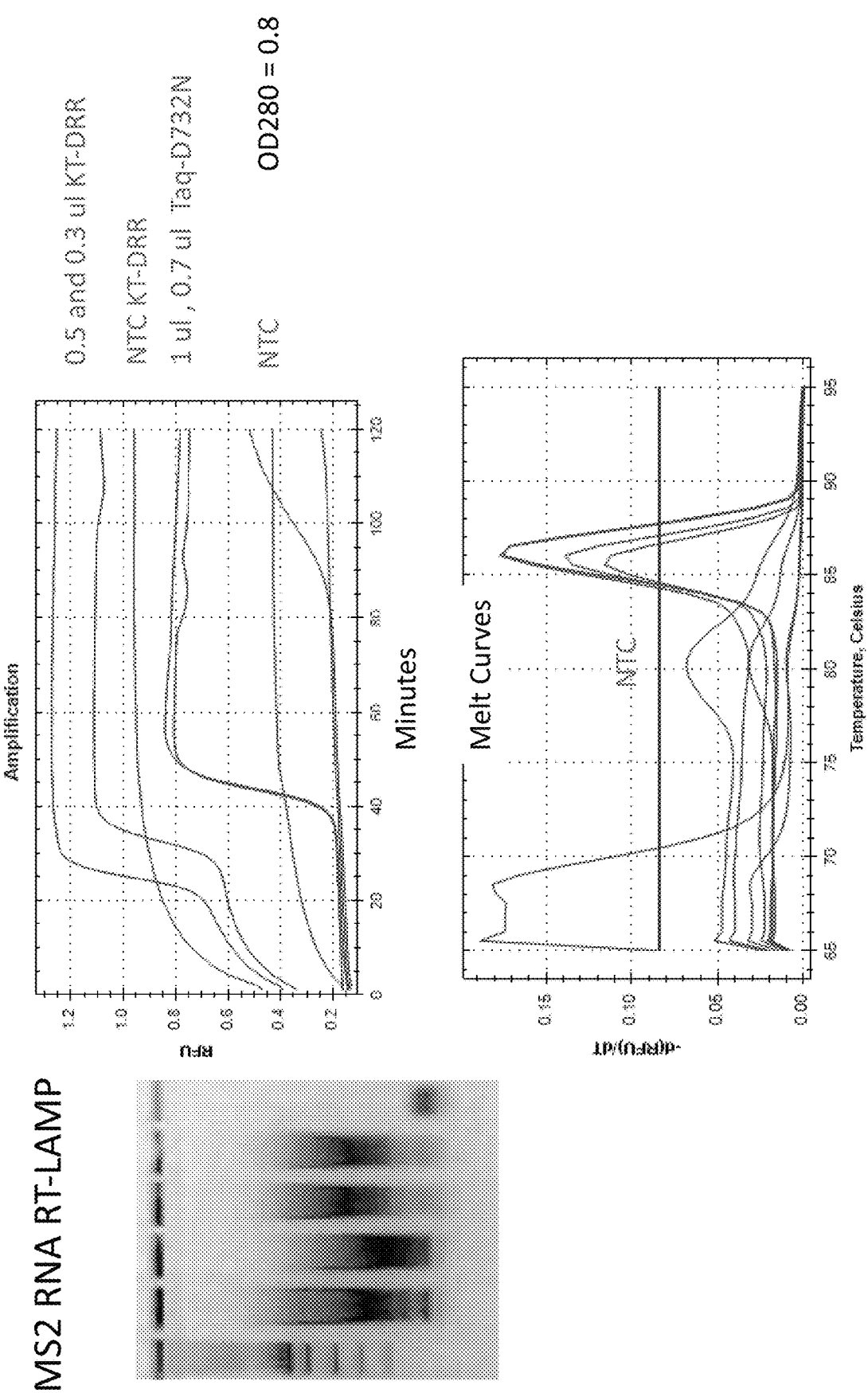

FIG. 15 shows a gel image, amplification curves and melt curves for an MS2 RNA RT-LAMP assay for KT-DRR (SEQ ID NO: 8), NTC KT-DRR, Taq-D732N (A111, SEQ ID NO: 3), and NTC.

Figure 16A:
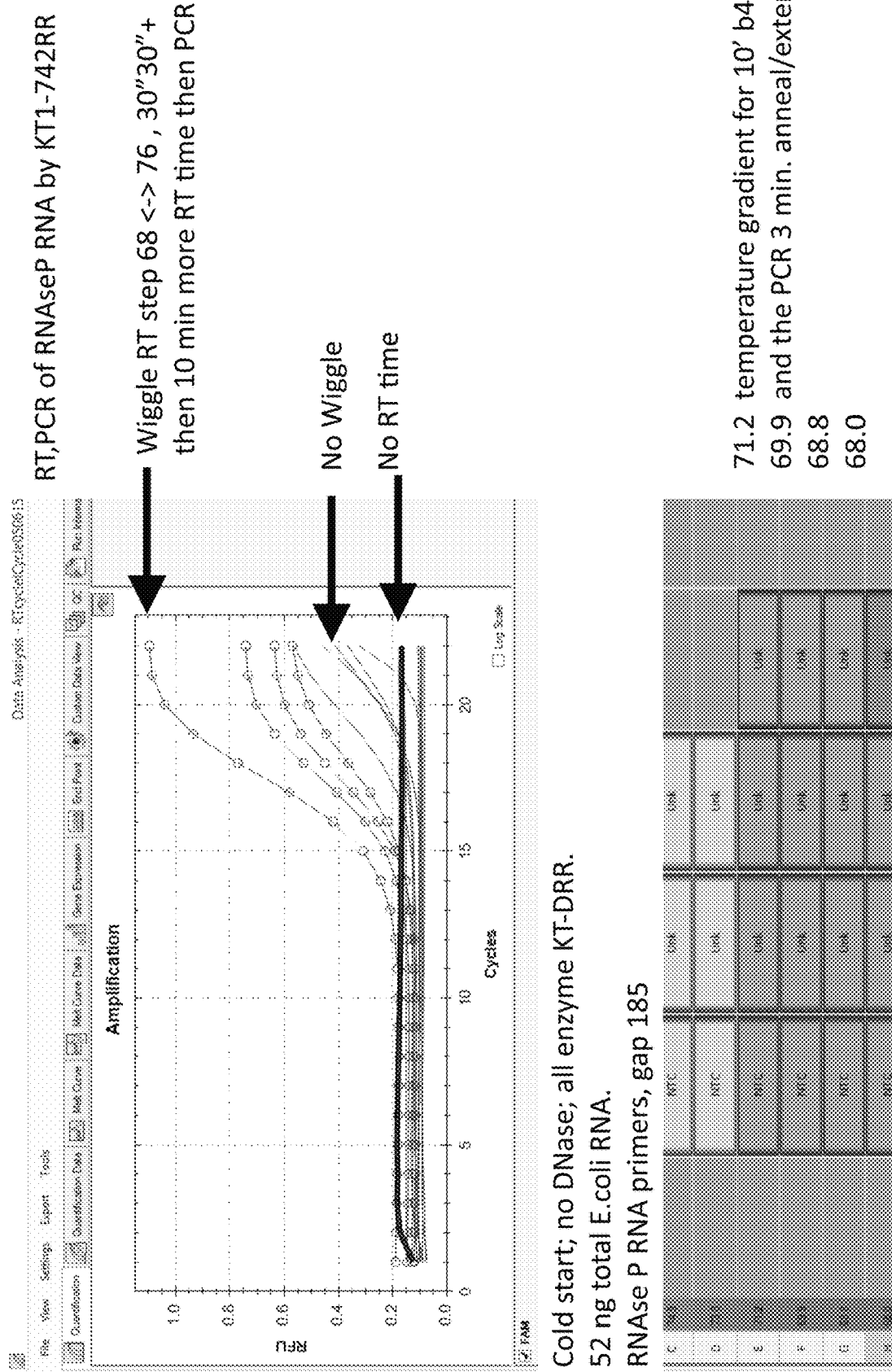
Figure 16B:
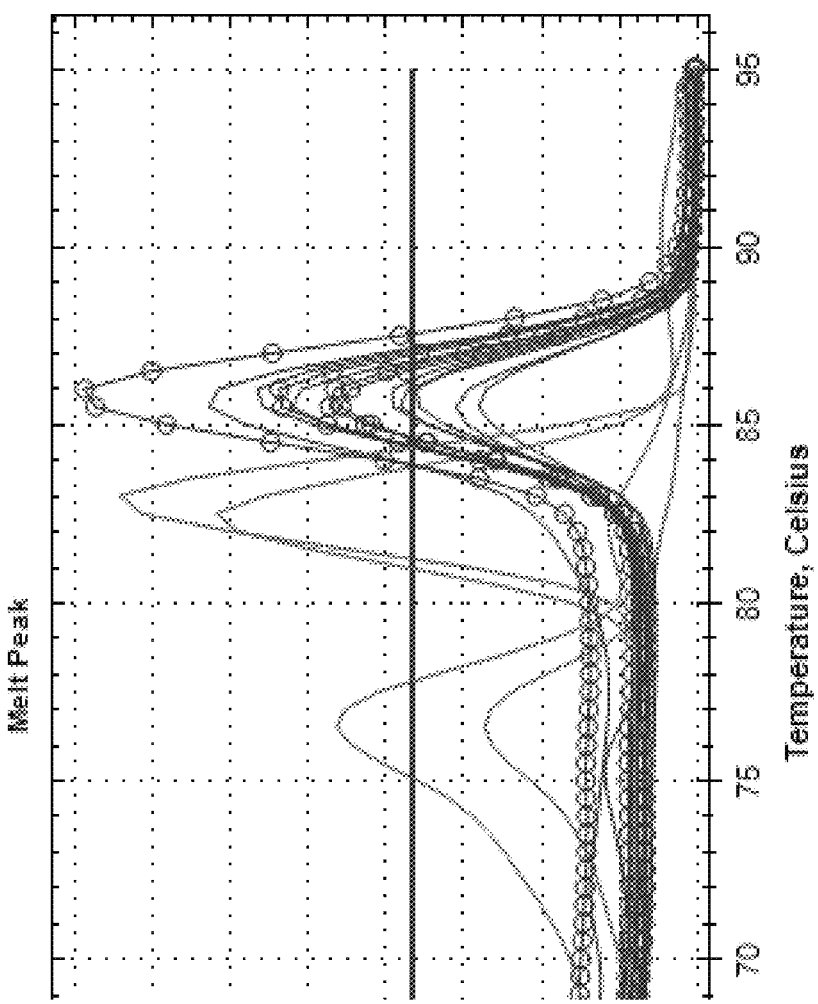

FIG. 16A-B shows amplification curves, melting curves and a diagram of temperature gradient for a RT-PCR assay. Results suggest that adding an RT step would be beneficial to provide some reaction time before the PCR starts. Results also showed improvements with "wiggle" of the temperature of this RT step.

Figure 17:
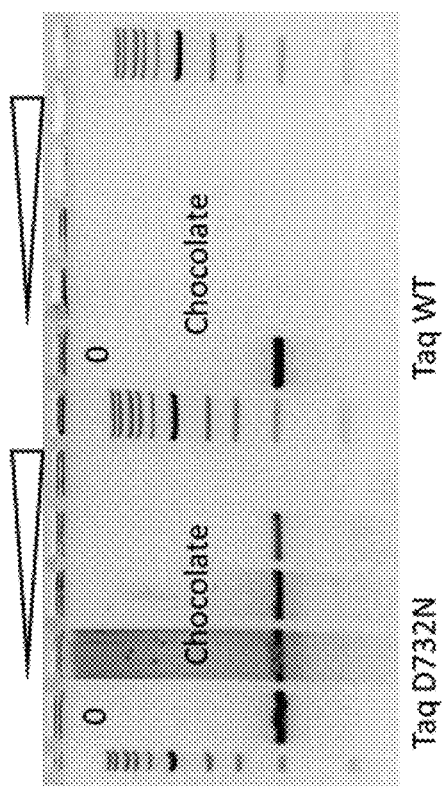

FIG. 17 shows ability of wild-type Taq and Taq mutant D732N to catalyze PCR reactions in the presence of various amount of chocolate.

Figure 18:
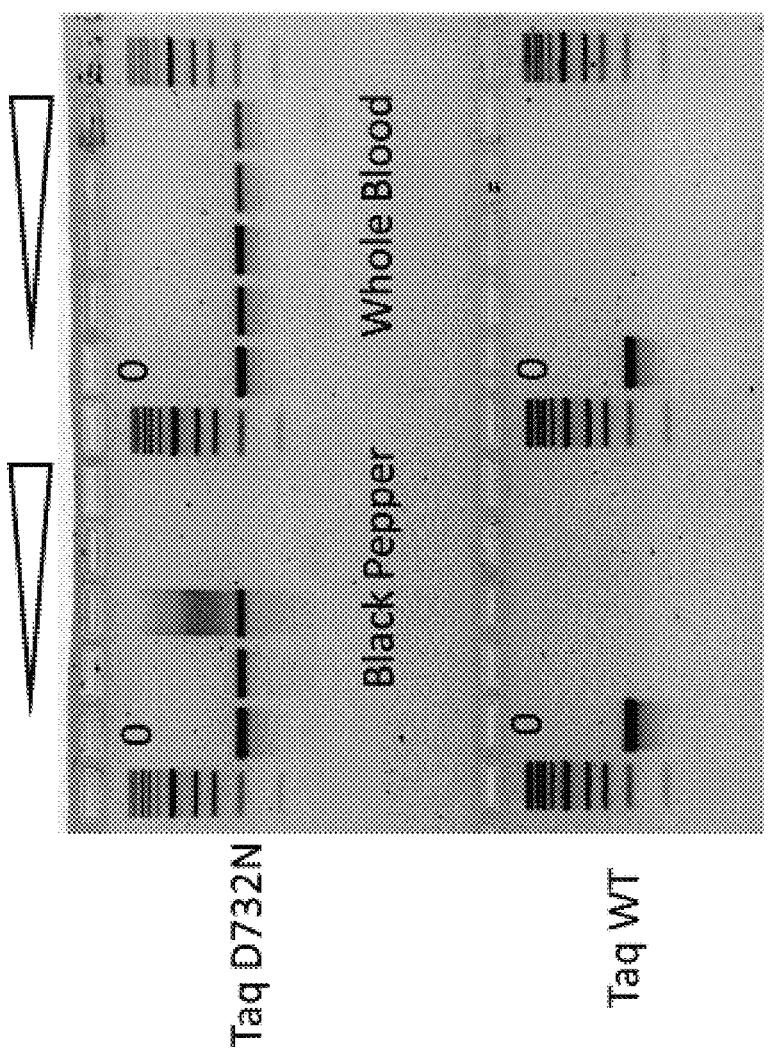

FIG. 18 shows the ability of wild-type Taq and Taq mutant D732N to catalyze PCR reactions in the presence of various amount of black pepper or whole blood.

Figure 19:
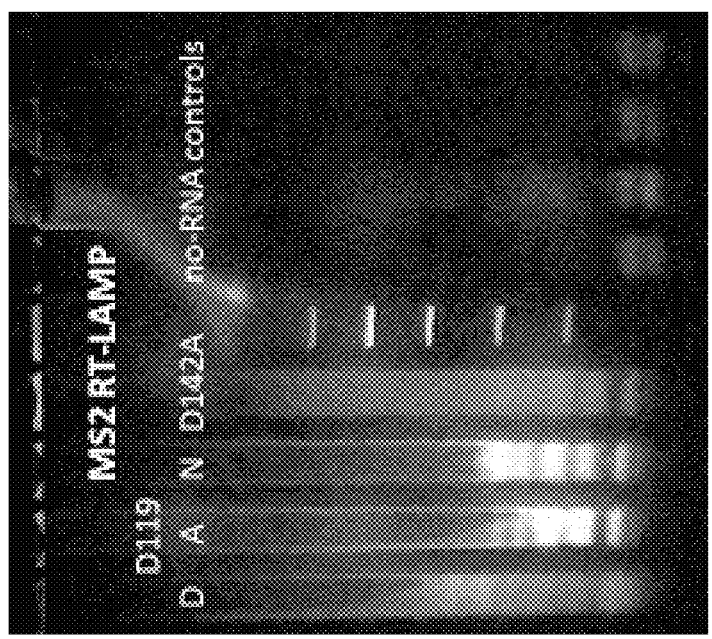

FIG. 19 shows the results of RT-LAMP with full-length Taq-D732N and 5'-exo mutations D119A and D119N.

Figure 20:
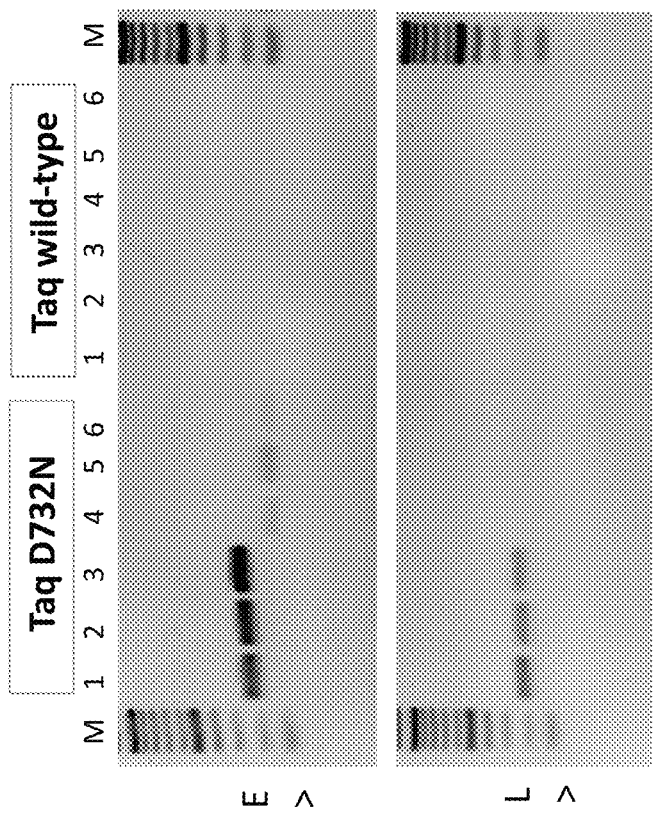

FIG. 20 shows the results of RT-PCR performed with Taq mutant D732N compared to wild-type Taq.

Figure 21:
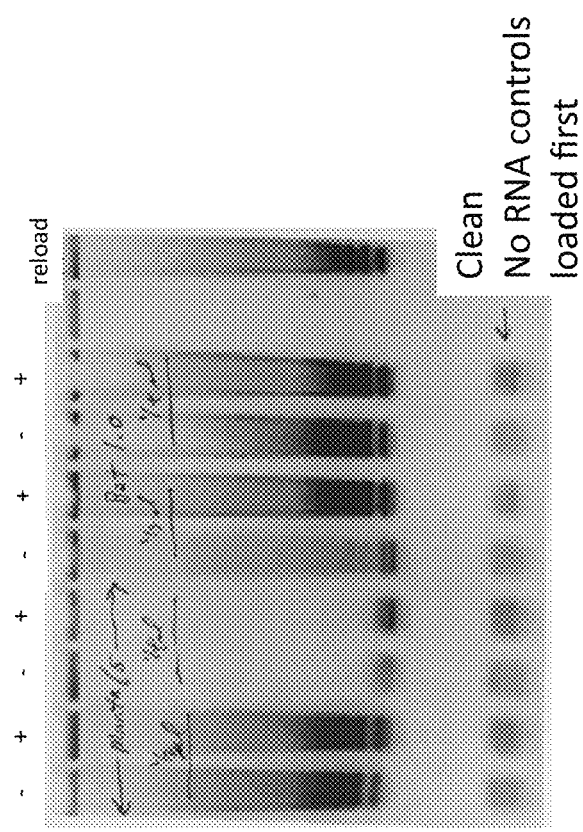

FIG. 21 shows that Bst DNA polymerase, without any RT (reverse transcriptase) enzyme, can catalyze RT-LAMP using the conditions described herein.

DETAILED DESCRIPTION OF THE INVENTION

The present disclosure is based, at least in part, on the discovery that a single mutation (D732N per wild type Taq numbering) of the PCR enzyme Klentaq1 DNA polymerase can broaden its ability to include multiple activities including reverse transcriptase (RT) activity or strand-displacement activity. As shown herein, a mutant Klentaq1 DNA polymerase having mutation D732N and RT and strand-displacement activity can catalyze reverse transcription loop-mediated isothermal amplification (RT-LAMP) using RNA template.

While a mutant polymerase having a D732N mutation has been associated with resistance to cracked pepper, chocolate, or blood (see e.g., U.S. Patent Application Publication No. 2014/0113299), the present disclosure is the first description of the surprising and unexpected RT and strand-displacement activity.

The present disclosure is based, at least in part, on a further discovery that mutations E742R and A743R (i.e., EA742RR) (optionally in combination with D732N) can reduce the amount of time to produce a typical DNA ladder from LAMP. As shown herein, while it can take 80-100 minutes using a polymerase having a D732N mutation at a constant 68° C. to produce the typical DNA ladder from LAMP with 1-2 ng of MS2 RNA template, a mutant polymerase having a D732N mutation and both E742R and A743R (EA742RR) mutations can reduce this time to 30-40 minutes.

While the combined E742R and A743R (EA742RR) polymerase mutation has been previously described and associated with showing higher DNA affinity or faster primer extension ability (see e.g., Yamagami et al. 2014 Front Microbiol 5:461), the present disclosure is the first description of the combination of the E742R, A743R, and D732N mutations and the surprising and unexpected RT and strand-displacement activity. Furthermore, Yamagami et al. (2014 Front Microbiol 5:461) described the combination of E742R and A743R (EA742RR) as "too tight" for useful PCR, thereby discouraging one of ordinary skill from using this mutation in a polymerase for PCR. But as disclosed herein, for strand-displacement activity, "tight" may be beneficial.

The present disclosure is based, at least in part, on a further discovery that mutations D119A or D119N (optionally in combination with D732N) can increase the clarity of the banding patterns for LAMP. As shown herein, a mutant polymerase having a D732N mutation and D119A or a mutant polymerase having a D732N mutation and D119N showed improved clarity (see e.g., FIG. 19).

As a further modification, a mutant polymerase having a D732N mutation; D732N, E742R, and A743R; D732N and D119A; or D732N and D119N; mutations can be combined with an insertion to allow fluorescent labeling with difluoro-F1AsH near the path of the DNA template. As shown herein, D732N, E742R, and A743R mutations were combined with an insertion FLNCCPGCC at 738,739 in a mutant polymerase to allow fluorescent labeling with difluoro-F1AsH near the path of the DNA template, for potential observation of single molecules of enzyme in action for a DNA sequencing method. As shown herein, without the F1AsH attachment, the mutant enzyme can still do PCR and RT-LAMP; in some embodiments, apparent activity can be reduced but still evident when the F1AsH is added.

The present disclosure is based, at least in part, on a further discovery of a method of RT-LAMP reliably dependent on the addition of MS2 RNA. It has been reported that performance of RT-LAMP can result in contamination of a surrounding environment with DNA product to the point that template is sometimes not required, or template RNA only enhances the appearance of product. Conventional solutions to this problem use 5 dNTPs G, A, C, T, and U coupled with eventual use of uracil deglycosylase.

A "hanging hot start" method using DNase I as disclosed can overcome reported RT-LAMP contamination issues. As shown herein, primers can be prepared and diluted in a non-contaminated environment, and added (e.g., in about 2-4 μl) to the cap of each reaction tube. The rest of the reaction (buffer, DNA polymerase, and MS2 RNA, etc.) can be set up (e.g., in about 23-25 μl) at the bottom of the reaction tube with RNase-free DNase I and $CaCl_2$ (e.g., about 0.1 mM) for a period of time (e.g., about 10-30 minutes) at a temperature (e.g., room temperature). The reaction tubes can be gently moved to a thermal cycler (which is not to be cycled) with the primers still hanging on the cap. After the block has warmed (e.g., to 68° C. or 75° C.) for a period of time (e.g., about 1 minute), the DNase I is inactive, and warm tubes can be removed from the hot block and mixed (e.g., flicked sharply downward to dislodge the primers into the reactions), then can be returned (e.g., returned immediately) to the hot block for incubation at a set temperature (e.g., 68° C.). With the above described protocol, RT-LAMP reactions can be reliably dependent on the addition of MS2 RNA, thereby overcoming in whole or in part the recognized contamination issues.

The following U.S. patent applications are incorporated herein by reference in their entirety: U.S. Pat. No. 7,462,475, issued 9 Dec. 2008; U.S. Patent Application Publication No. 2009/0170060, published 2 Jul. 2009; U.S. Patent Application Publication No. 2011/0027832, published 3 Feb. 2011; U.S. Patent Application Publication No. 2012/0028259, published 2 Feb. 2012; international PCT application WO2012/088479, published 28 Jun. 2012; and U.S. Patent Application Publication No. 2014/0113299, published 24 Apr. 2014. Except as otherwise noted herein, therefore, the process of the present disclosure can be carried out in accordance with compositions or processes of these references.

Mutant Polymerases

Some embodiments provide mutant polymerases having polymerase activity, reverse transcriptase activity (RT), or strand-displacement activity. For example, some mutant polymerases described herein have polymerase activity, RT activity, and strand-displacement activity. Such mutant polymerases can be used in, e.g., RT-PCR, LAMP PCR, or RT-LAMP PCR.

According to conventional notation, amino acid mutations discussed herein may be represented, from left to right, by the one letter code for the wild type amino acid, the amino acid position number, and the one letter code for the mutant amino acid. For mutant polypeptide sequences, an amino acid different than corresponding wild type may be represented, from left to right, by the amino acid position number and the one letter code for the amino acid that is different than corresponding wild type.

A "variant" polypeptide described in the following paragraphs is as defined in the "variant" section further below. Exemplary sequence identity (e.g., at least about 95% sequence identity) is not meant to limit the full range of sequence identity as discussed in the "variant" section herein.

For the following discussion, wild type Taq numbering (corresponding to numbering of full-length Taq of SEQ ID NO: 1) is used in this descriptive text so as to make clear the relationship between the polypeptides. Wild type Taq (SEQ ID NO: 1) and truncated Klentaq-1 (SEQ ID NO: 2) have complete sequence homology across positions 279-832 of SEQ ID NO: 1, except for positions 279 (Gly) and 280 (Ser) of SEQ ID NO: 1 (corresponding to positions 1 (Met) and 2 (Gly) of truncated SEQ ID NO: 2). Klentaq-1 (SEQ ID NO: 2) has an open reading frame sequence starting with codons for amino acids methionine (M), glycine (G), leucine (L), leucine (L), histidine (H), glutamic acid (E), phenylanine (F). The amino acid changes at 279-280 of wild type Taq (SEQ ID NO: 1) and positions 1-2 of truncated Klentaq-1 (SEQ ID NO: 2) are not necessarily associated with a difference in phenotype as described herein.

With respect to wild-type Taq numbering, for truncated polymerase polypeptides (e.g., Klentaq-1 of SEQ ID NO: 2), position number 1 as notated in the Sequence Listing of SEQ ID NO: 2 corresponds to position number 279 as notated in the full-length Taq of SEQ ID NO: 1. Similarly, position number 2 of SEQ ID NO: 2 corresponds to position number 280 of SEQ ID NO: 1. Similarly, position number 454 of SEQ ID NO: 2 corresponds to position number 732 of SEQ ID NO: 1. Similarly, position number 464 of SEQ ID NO: 2 corresponds to position number 742 of SEQ ID NO: 1. Similarly, position number 465 of SEQ ID NO: 2 corresponds to position number 743 of SEQ ID NO: 1. In other words, one can determine the corresponding position in full-length SEQ ID NO: 1 by adding 278 the any position in SEQ ID NO: 2.

A mutant polymerase described herein can be produced according to methods known in the art. For example, oligonucleotides providing the specific amino acid changes to a mutant polymerase described can be prepared by standard synthetic techniques (e.g., an automated DNA synthesizer) and used as PCR primers in site-directed mutagenesis. Standard procedures of expression of mutant polymerase polypeptides from encoding DNA sequences can then be performed. Alternatively, the mutant DNA polymerase polypeptides can be directly synthesized according to methods known in the art.

A mutant polymerase having a mutation described herein can be a full length mutant polymerase or a truncated mutant polymerase, as compared to a wild-type Taq polymerase. For example, a truncated mutant polymerase can be truncated at position 278 per wild-type Taq numbering (e.g., position 1 of the truncated mutant corresponds to position 279 of SEQ ID NO: 1). One of skill in the art will understand that a truncated mutant polymerase can be truncated at any position of a full length sequence so long as polymerase activity (or other required phenotypes, such as RT activity or strand-displacement activity) is retained.

A truncated mutant polymerase can be referred to as a "functional fragment" of a longer polymerase, such as a full-length polymerase. For example, SEQ ID NO: 2 (Klentaq-1, KT-1) is a variant (having G279M and S280G per wild type Taq numbering) and functional fragment of SEQ ID NO: 1 (wild type Taq). A functional fragment is shorter than the length of a reference polymerase and retains polymerase activity (or other required phenotypes, such as RT activity or strand-displacement activity).

As disclosed herein, one or more amino acid mutations (e.g., addition, deletion, substitution) can be associated with a phenotype described herein. In some embodiments, a mutant polymerase (e.g., a full length mutant polymerase or a truncated mutant polymerase) can include one or more of mutations D732N, E742R, or A743R. For example, a mutant polymerase (e.g., a full length mutant polymerase or a truncated mutant polymerase) can include mutation D732N. As another example, a mutant polymerase (e.g., a full length mutant polymerase or a truncated mutant polymerase) can include mutations E742R and A743R. As another example, a mutant polymerase (e.g., a full length mutant polymerase or a truncated mutant polymerase) can include mutations D732N, E742R, and A743R. The combination of E742R and A743R can also be referred to herein as EA742RR.

For example, a mutant polymerase can include an amino acid sequence of SEQ ID NO: 1 having a D732N substitution, or a variant (e.g., at least about 95% sequence identity) thereof having at least the D732N substitution and having polymerase activity and RT activity or strand displacement activity. A full length mutant polymerase having a D732N substitution can be mutant polymerase A-111 as identified in U.S. Patent Application Publication No. 2014/0113299. As demonstrated, full length A-111 having D732N (SEQ ID NO: 3) can overcome enzyme inhibitors in chocolate, pepper and cheese, thereby reducing or eliminating purification of food or food-bacteria culture RNA or DNA.

Full length A-111 having D732N (SEQ ID NO: 3) can show smearing on an agarose gel when tested for normal PCR with longer products. This may be due to higher than normal template-switching, in which a strand-displacing enzyme would be expected to be good at. Full length A-111 having D732N (SEQ ID NO: 3) can reduce maximum yield of PCR product with a reduced amount of input template.

As another example, a mutant polymerase can include an amino acid sequence of SEQ ID NO: 2 having a D732N mutation (per wild-type Taq numbering), or a variant (e.g., at least about 95% sequence identity) thereof having at least the D732N substitution and having polymerase activity and RT activity or strand displacement activity. Note that D454 in SEQ ID NO: 2 corresponds to D732 according to wild type Taq numbering.

As another example, a mutant polymerase can include an amino acid sequence of SEQ ID NO: 1 having a E742R substitution and a A743R substitution (which can be referred to as EA742RR), or a variant (e.g., at least about 95% sequence identity) thereof having at least the E742R and A743R substitutions and having polymerase activity and RT activity or strand displacement activity.

As another example, a mutant polymerase can include an amino acid sequence of SEQ ID NO: 2 having an E742R substitution and an A743R substitution (per wild-type Taq numbering), or a variant (e.g., at least about 95% sequence identity) thereof having at least the E742R and A743R substitutions and having polymerase activity and RT activity or strand displacement activity. Note that E464 of SEQ ID NO: 2 corresponds to E742 according to wild type Taq numbering; and A465 of SEQ ID NO: 2 corresponds to A743 according to wild type Taq numbering. As shown herein, a Klentaq1 double mutant having E742R and A743R substitutions (EA742RR) can requires the use of less enzyme, provides faster results, and functions in the presence of inhibitors.

As another example, a mutant polymerase can include an amino acid sequence of SEQ ID NO: 1 having a D732N substitution, a E742R substitution, and a A743R substitution, or a variant (e.g., at least about 95% sequence identity) thereof having at least the D732N, E742R, and A743R substitutions and having polymerase activity and RT activity or strand displacement activity.

As another example, a mutant polymerase can include an amino acid sequence of SEQ ID NO: 2 having a D732N substitution, a E742R substitution, and a A743R substitution (per wild-type Taq numbering), or a variant (e.g., at least about 95% sequence identity) thereof having at least the D732N, E742R, and A743R substitutions and having polymerase activity and RT activity or strand displacement activity. Note that D454 in SEQ ID NO: 2 corresponds to D732 according to wild type Taq numbering; E464 of SEQ ID NO: 2 corresponds to E742 according to wild type Taq numbering; and A465 of SEQ ID NO: 2 corresponds to A743 according to wild type Taq numbering.

A mutant polymerase described herein can further include a polymerase mutation disclosed in U.S. Pat. Nos. 6,403,341; 7,393,635; 7,462,475; WO 2012/088479 (and corresponding U.S. application Ser. No. 13/997,194); US Pat App Pub No. 2010/0013291; US Pat App Pub No. 2012/0028259, and US Pat App Pub No. 2014/0113299, each incorporated herein by reference.

In some embodiments, a mutant polymerase (e.g., a full length mutant polymerase or a truncated mutant polymerase) can include one or more of the following substitutions: L609P, E626K, V649I, I707L, E708K, E708L, E708N, E708Q, E708I, E708W, E708R, E708V, E708S, E404G, G418E, V453L, A454S, R487G, I528ML533R, D551G, D578E, I599V, L657Q, K738R, L781 I, or E818V (per wild type numbering). A substitution at one or more of these positions (e.g., 708) can occur in combination with one or more other substitutions described herein. For example, a mutant polymerase (e.g., a full length mutant polymerase or a truncated mutant polymerase) can have (A) one or more substitutions selected from D732N, E742R, and A743R and (B) at least one substitution selected from L609P, E626K, V649I, I707L, E708K, E708L, E708N, E708Q, E708I, E708W, E708R, E708V, E708S, E404G, G418E, V453L, A454S, R487G, I528ML533R, D551G, D578E, I599V, L657Q, K738R, L781 I, and E818V (per wild type numbering). As another example, a mutant polymerase can include SEQ ID NO: 1 having (A) one or more substitutions selected from D732N, E742R, and A743R and (B) at least one substitution selected from L609P, E626K, V649I, I707L, E708K, E708L, E708N, E708Q, E708I, E708W, E708R, E708V, E708S, E404G, G418E, V453L, A454S, R487G, I528ML533R, D551G, D578E, I599V, L657Q, K738R, L781I, and E818V (per wild type numbering). As another example, a mutant polymerase can include SEQ ID NO: 2 having (A) one or more substitutions selected from D732N, E742R, and A743R (per wild-type Taq numbering) and (B) at least one substitution selected from L609P, E626K, V649I, I707L, E708K, E708L, E708N, E708Q, E708I, E708W, E708R, E708V, E708S, E404G, G418E, V453L, A454S, R487G, I528ML533R, D551G, D578E, I599V, L657Q, K738R, L781 I, and E818V (per wild-type Taq numbering).

A mutant polymerase described herein can be used in conjunction with compositions or processes described in U.S. Pat. Nos. 6,403,341; 7,393,635; 7,462,475; WO 2012/088479 (and corresponding U.S. application Ser. No. 13/997,194); US Pat App Pub No. 2010/0013291; US Pat App Pub No. 2012/0028259, and US Pat App Pub No. 2014/0113299, each incorporated herein by reference.

Another aspect of the present disclosure provides a polynucleotide encoding a mutant polymerase described herein. Also provided is a nucleic acid construct (e.g., an expression vector) including polynucleotide encoding a mutant polymerase described herein. A construct (e.g., a DNA construct) can include the following operably associated components: a promoter functional in a host cell, a nucleotide sequence (e.g., a heterologous DNA sequence, an exogenous DNA segment, or a heterologous nucleic acid) encoding a mutant polymerase described herein, a transcriptional termination sequence. Generation of an encoding polynucleotide, a nucleic acid construct (e.g., an expression vector), transformation of a host cell with such construct, and expression of a mutant polymerase from a transformed host cell is within the state of the art.

Variants

The term "variant" polypeptides (or encoding polynucleotides) is discussed below. The description of "variant" below is incorporated by reference into each recitation of "variant" in the description of mutant polymerases herein. For example, the full range of sequence identity discussed below applies equally to "variant" polypeptides discussed elsewhere herein.

Included in the scope of the present disclosure are variant polypeptides (or encoding polynucleotides) with at least 80% sequence identity to sequences described herein, so long as such variants retain (A) a polymerase activity and (B) RT activity or strand displacement activity.

For example, a variant polypeptide (or an encoding polynucleotide) with polymerase activity can have at least about 85%, 86%, 87%, 88%, 89%, 90%, 91%, 92%, 93%, 94%, 95%, 96%, 97%, 98%, 99%, or 99.9% sequence identity to sequences disclosed herein (including disclosed sequences having substitutions described herein). It is understood that in some embodiments, "about" modifies each of these recited sequence identity values. A variant polypeptide (or encoding polynucleotides) with polymerase activity, RT activity, or strand displacement activity can have at least 95% sequence identity to a sequence disclosed herein. A variant polypeptide (or an encoding polynucleotide) with polymerase activity, RT activity, or strand displacement activity can have at least 99% sequence identity to a sequence disclosed herein. The species are representative of the genus of variant polypeptides of each of these respective sequences because all variants must possess the specified catalytic activity (e.g., polymerase activity, RT activity, or strand displacement activity) and must have the percent identity required above to the reference sequence.

Design, generation, and testing of the variant polypeptides having the above required percent identities to the sequences of the mutant DNA polymerases and retaining a required resistant phenotype is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of polypeptide variants having, for example, at least 95-99% identity to the sequences of mutant DNA polymerases described herein and screen such for phenotypes including, dye-resistance, blood-resistance, or soil-resistance according to methods routine in the art. Generally, conservative substitutions can be made at any position so long as the required activity is retained.

Amino acid sequence identity percent (%) is understood as the percentage of amino acid residues that are identical with amino acid residues in a candidate sequence in comparison to a reference sequence when the two sequences are aligned. To determine percent amino acid identity, sequences are aligned and if necessary, gaps are introduced to achieve the maximum percent sequence identity; conservative substitutions are not considered as part of the sequence identity. Amino acid sequence alignment procedures to determine percent identity are well known to those of skill in the art. Often publicly available computer software, such as BLAST, BLAST2, ALIGN2 or Megalign (DNASTAR) software, is used to align peptide sequences. Those skilled in the art can determine appropriate parameters for measuring alignment, including any algorithms needed to achieve maximal alignment over the full-length of the sequences being compared. When amino acid sequences are aligned, the percent amino acid sequence identity of a given amino acid sequence A to, with, or against a given amino acid sequence B (which can alternatively be phrased as a given amino acid sequence A that has or comprises a certain percent amino acid sequence identity to, with, or against a given amino acid sequence B) can be calculated as: percent amino acid sequence identity=X/Y100, where X is the number of amino acid residues scored as identical matches by the sequence alignment program's or algorithm's alignment of A and B, and Y is the total number of amino acid residues in B. If the length of amino acid sequence A is not equal to the length of amino acid sequence B, the percent amino acid sequence identity of A to B will not equal the percent amino acid sequence identity of B to A.

Phenotype

As described herein, a mutant polymerase described herein can have polymerase activity, RT activity, or strand displacement activity. As described herein, a mutant polymerase can be multi-functional. For example, a mutant polymerase can be bifunctional. Bifunctionality can include polymerase activity and either RT activity or strand displacement activity, and therefore have PCR and LAMP functionality.

Polymerase Activity.

A polymerase enzyme is understood to a add a free nucleotide to an —OH group on the 3' end of a newly forming nucleic acid strand, resulting in elongation of the strand in a 5'-3' direction. Directionality of the newly forming strand (the daughter strand) is understood to be opposite to the direction in which a polymerase moves along a template strand. Thus, a polymerase moves along the template strand in a 3'-5' direction, and the daughter strand is formed in a 5'-3' direction. In some embodiments, polymerase activity includes the ability of a polymerase to fully or partially complete a PCR. PCR is described further below.

In some embodiments, a polymerase activity is a resistant polymerase activity, where the mutant polymerase is resistant to one or more substances that can inhibit PCR. A mutant polymerase described herein can have a phenotype including polymerase activity and an ability to fully or partially complete a PCR in a reaction mixture including an inhibitory substance at a concentration that a control polymerase (e.g., wild type Taq polymerase of SEQ ID NO: 1, or Klentaq1 polymerase of SEQ ID NO: 2) would fail to amplify a target nucleic acid. Resistant polymerase activity can be retention of all or most polymerase activity, or sufficient polymerase to complete a PCR, in the presence of a sample containing one or more of chocolate, pepper, milk, seafood, meat, egg, blood, urine, humic acid, bile, or plant material in sufficient quantity to inhibit or substantially inhibit a corresponding wild type polymerase. A mutant polymerase described herein can have a phenotype including polymerase activity and an ability to fully or partially complete a PCR in a reaction mixture including an inhibitory substance at a concentration that a control (e.g., wild type Taq polymerase of SEQ ID NO: 1 or Klentaq1 of SEQ ID NO: 2) would fail to amplify a target nucleic acid. An inhibitory substance can be present in food or food samples, such as chocolate, peanut butter, milk, seafood, meat, or egg, or other foods or food samples. GITC (guanidinium) or ethanol are exemplary inhibitory substance that can be present in an assay mixture. An inhibitory substance can be present in chocolate, pepper, blood, urine, humic acid, bile, tannins, melanin, indigo dyes, or plant material. For example, an inhibitory substance can be a polyphenol, such as a polyphenol present in a sample described above. Thus, a mutant polymerase described herein can be used to amplify a target polynucleotide in a PCR in the presence of one or more inhibitory substances.

Generally, a mutant polymerase having a resistant polymerase activity described herein can tolerate at least an order of magnitude greater concentration of an inhibitory substance described herein as compared to a control (e.g., wild type Taq polymerase of SEQ ID NO: 1 or Klentaq1 of SEQ ID NO: 2). A mutant polymerase described herein can provide for amplification of a target nucleic acid in a sample containing an inhibitory substance at a level inhibitory to a wild type Taq, Klentaq, Omni Taq, or Omni Klentaq.

Reverse Transcriptase Activity.

Reverse transcriptase (RT) activity can create a single-stranded complementary DNA (cDNA) from an RNA template.

RT activity can allow reverse transcription of a target RNA into its DNA complement. The newly synthesized cDNA can used as a template for amplification using PCR or LAMP, or another DNA amplification protocol.

RT activity can be measured in a variety of protocols known to the art (see e.g., King and O'Connel (2002) RT-PCR Protocols, $1^{st}$ Ed., Human Press, ISBN-10 0896038750; Blotter et al. 2013 Angewandte Chemie International Edition 52, 11935-11939; Ong et al. 2006 Journal of Molecular Biology 361, 537-550; Example 1; Example 2).

While other studies have identified different combinations of four amino acid changes that demonstrate reverse transcriptase activity for Klentaq1 (Blatter et al. 2013 Angewandte Chemie International Edition 52, 11935-11939) or Taq DNA polymerase (Ong et al. 2006 Journal of Molecular Biology 361, 537-550), such mutations are different from and do not overlap mutations disclosed herein.

Strand Displacement Activity.

A phenotype of a mutant polymerase described herein can have polymerase activity (or resistant polymerase activity) and RT activity or strand displacement activity.

Strand displacement activity can be measured in a variety of protocols known to the art (see e.g., Example 1; Example 2).

Given the well-known lack of strand displacement activity in Taq (SEQ ID NO: 1) or Klentaq1 (SEQ ID NO: 2), strand-displacement and LAMP catalysis associated with mutation D732N was a very surprising discovery.

Mechanism

While under no obligation to do so, and in no way limiting the scope of the present disclosure, the following discussion is directed to mechanism of action. The location of the D732N mutation is neither near the active site nor near the DNA in the published crystal structures with primer and template. It is presently thought that the D732N mutation may be near the displaced DNA strand during strand-displacement, or the incoming RNA template may track in differently than does DNA template in the crystal structures. This location, or near it, can be a newly reasonable place to put a fluorescent probe of template-strand bases.

Although mutation D732N appears distant from the primer and template strand in the crystal structures, strand-displacement involves three strands, and there is yet no information about the track taken by the displaced strand. The single-strand template takes a surprising right turn near 742,743 in the Bst crystal structure 1L3S, so the displaced strand could also be in this area, since it was just recently unpaired from the template strand. That could put it near amino acid residue 732 (per wild type Taq numbering). Consistent with this reasoning, Klentaq1 (SEQ ID NO: 2) has a positively charged surface RRR (and Bst has KQK) in the spatially extrapolated position at 715-717 where positively charged residues could interact with phosphates of the displaced strand, if it is still close to the enzyme.

PCR

A mutant polymerase (including all variants thereof) described herein can be used in a variety of polymerase reactions known to the art (see e.g., Dorak (2006) Real-Time PCR, Taylor & Francis, ISBN 041537734X; Bustin, ed. (2004) A-Z of Quantitative PCR, International University Line, ISBN 0963681788; King and O'Connel (2002) RT-PCR Protocols, $1^{st}$ Ed., Human Press, ISBN-10 0896038750). For example, a mutant polymerase can be employed in PCR reactions, primer extension reactions, etc.

For example, a mutant polymerase described herein can be used in nucleic acid amplification processes (either alone or in combination with one or more other enzymes), such as Allele-specific PCR; Assembly PCR or Polymerase Cycling Assembly; Asymmetric PCR; Linear-After-The-Exponential-PCR; Helicase-dependent amplification; Hot-start-PCR; Intersequence-specific PCR; Inverse PCR; Ligation-mediated PCR; Methylation-specific PCR; Miniprimer PCR; Multiplex Ligation-dependent Probe Amplification; Multiplex-PCR; Nested PCR; Overlap-extension PCR; Quantitative PCR; Quantitative End-Point PCR; Quantitative Real-Time PCR; RT-PCR (Reverse Transcription PCR); loop-mediated isothermal amplification (LAMP), reverse transcriptase loop-mediated isothermal amplification (RT-LAMP), Solid Phase PCR; Thermal asymmetric interlaced PCR; Touchdown PCR; PAN-AC; Universal Fast Walking; Long PCR; Rapid Amplified Polymorphic DNA Analysis; Rapid Amplification of cDNA Ends (RACE); Differential Display PCR; In situ PCR; High-Fidelity PCR; PCR or DNA Sequencing (cycle sequencing).

A target nucleic acid of a sample can be any target nucleic acid of interest. For example, a target nucleic acid can be a deoxyribonucleic acid (DNA), a ribonucleic acid (RNA), or an artificial nucleic acid analog (e.g., a peptide nucleic acid, morpholino- and locked nucleic acid, glycol nucleic acid, or threose nucleic acid).

A primer is understood to refer to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, e.g., in the presence of four different nucleotide triphosphates and thermostable enzyme in an appropriate buffer ("buffer" includes pH, ionic strength, cofactors, etc.) and at a suitable temperature. The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the thermostable enzyme. The exact lengths of the primers will depend on many factors, including temperature, source of primer and use of the method. For example, depending on the complexity of the target sequence, the oligonucleotide primer typically contains 15-25 nucleotides, although it may contain more or few nucleotides. Short primer molecules generally require colder temperatures to form sufficiently stable hybrid complexes with template.

A target nucleic acid, e.g., a template DNA molecule, is understood to be a strand of a nucleic acid from which a complementary nucleic acid strand can be synthesized by a DNA polymerase, for example, in a primer extension reaction.

A mutant polymerase described herein can be used in an end-point PCR. For example, end-point PCR is commonly carried out in a reaction volume of about 10-200 µl in small reaction tubes (about 0.2-0.5 ml volumes) in a thermal cycler. A mutant polymerase described herein can be used with a variety of commercially available end-point PCR kits. The use of a mutant polymerase enzyme described herein generally does not require any, or substantial, changes in the typical end-point PCR protocol, but can allow, for example, a sample having a higher amount of an inhibitory substance.

A mutant polymerase described herein can be used in real-time PCR (also known as a quantitative polymerase chain reaction (qPCR)). For example, a mutant polymerase described herein can be used in a real-time PCR assay featuring a non-specific fluorescent dye (e.g., a fluorochrome) that can intercalate with any double-stranded DNA. With a non-specific fluorescent dye, an increase in DNA product during PCR can lead to an increase in fluorescence intensity and is measured at each cycle, thus allowing DNA concentrations to be quantified.

As another example, a mutant polymerase described herein can be used in a real-time PCR assay featuring a hybridization probe. As another example, a mutant polymerase described herein can be used in a real-time PCR multiplex assay featuring a hybridization probe. A hybridization probe can be a sequence-specific DNA probe including a fluorescent reporter at one end and a quencher of fluorescence at the opposite end of the probe, where break down of the probe by a 5' to 3' exonuclease activity of a polymerase can break the reporter-quencher proximity and thus allow unquenched emission of fluorescence, which can be detected after excitation with a laser (e.g., a TaqMan® assay). With a hybridization probe, an increase in the product targeted by the reporter probe at each PCR cycle can cause a proportional increase in fluorescence due to the breakdown of the probe and release of the reporter. A mutant polymerase described herein can be used with a variety of commercially available real-time PCR kits.

RT-PCR.

As another example, a mutant polymerase described herein can be used Reverse Transcriptase (RT) PCR. In some embodiments, the use of a mutant polymerase enzyme described herein does not require any, or substantial, changes in the typical protocol, but can allow, for example, exclusion of a reverse transcriptase enzyme from a Reverse-Transcriptase (RT) PCR.

In some embodiments, the use of a mutant polymerase enzyme described herein does not require any, or substantial, changes in the typical protocol, but can allow, for example, exclusion of a reverse transcriptase enzyme from a Reverse-Transcriptase (RT) PCR in an amount sufficient to generate cDNA from an RNA template or in an amount sufficient to initiate reverse transcription.

A mutant polymerase described herein can be used in a variety of RT-PCR protocols known to the art (see e.g., King and O'Connel (2002) RT-PCR Protocols, $1^{st}$ Ed., Human Press, ISBN-10 0896038750). The use of the mutant polymerase enzymes described herein generally does not require any, or substantial, changes in the typical protocol, other than, for example, being able to eliminate a separate reverse transcriptase enzyme from the reaction mixture.

Conventionally, RT-PCR can be achieved as either a one-step or a two-step reaction. In the one-step approach, the entire reaction from cDNA synthesis to PCR amplification can occur in a single tube. The conventional two-step reaction can require that the reverse transcriptase reaction and PCR amplification be performed in separate tubes. Mutant polymerases described herein can be used in a one-step reaction or a two-step reaction. For example, a mutant polymerase described herein can be used in a one-step RT-PCR. As another example, a mutant polymerases described herein can be used in a two-step RT-PCR.

An exemplary RT-PCR is described below. In some embodiments, a one-step RT-PCR can take mRNA targets (e.g., up to 6 kb) and subject them to reverse transcription and then PCR amplification in a single test tube. A sequence-specific primer can be selected. A reaction mixture is prepared, including, e.g., dNTPs, primers, template RNA, necessary enzymes and a buffer solution. According to the present disclosure, a mutant polymerase described herein can have both DNA polymerase activity and reverse transcriptase activity, which can eliminate the need for two separate enzymes. The reaction mixture can be added to a PCR tube for each reaction, to which can be added template RNA. PCR tubes can be placed in a thermal cycler to begin cycling. The first cycle can be reverse transcription to synthesize cDNA. The (optional) second cycle can be initial denaturation. Conventionally, the denaturation step can inactivate a reverse transcriptase enzyme but a mutant polymerase disclosed herein can be resistant to such denaturation and so, the step may not be necessary. The next cycles (e.g., 40 to 50) can be an amplification program, consisting of three steps: denaturation, annealing, elongation. The RT-PCR products can then be analyzed according to conventional techniques (e.g., gel electrophoresis).

An RT-PCR can be an end-point RT-PCR or a real-time RT-PCR. Conventional RT-PCR protocols, such as end-point RT-PCR or real-time RT-PCR, can be used in combination with, or adapted to, mutant polymerases and methods described herein.

An end-point RT-PCR can require the detection of target nucleic acid levels by the use of, e.g., fluorescent dyes like ethidium bromide, P32 labeling of PCR products using phosphorimager, or by scintillation counting. End-point RT-PCR can be achieved using three different methods: relative, competitive and comparative. Relative quantifications of RT-PCR can involve the co-amplification of an internal control simultaneously with the gene of interest. The internal control can be used to normalize the samples. Competitive RT-PCR technique can be used for absolute quantification, and can use a synthetic "competitor" RNA that can be distinguished from the target RNA by a small difference in size or sequence. Comparative RT-PCR is similar to competitive RT-PCR in that the target RNA competes for amplification reagents within a single reaction with an internal standard of unrelated sequence.

Real-time RT-PCR can use fluorescent DNA probes (e.g., SYBR Green, TaqMan, Molecular Beacons, or Scorpions).

It is noted that reverse transcriptase (RT) PCR is not to be confused with real-time polymerase chain reaction (Q-PCR), which is sometimes (incorrectly) abbreviated as RT-PCR in the art. In RT-PCR, an RNA strand is first reverse transcribed into its DNA complement (complementary DNA, or cDNA) using the enzyme reverse transcriptase, and the resulting cDNA is amplified using traditional PCR. Like with end-point PCR, conventional RT-PCR protocols require extensive purification steps prior to amplification to purify RNA from inhibitors and ribonucleases, which can destroy the RNA template. Both the inhibition and degradation of RNA are major concerns in important clinical and diagnostics tests, which may lead to false-negative results.

Applications of RT-PCR include, but are not limited to, detection of RNA virus pathogens; analysis of mRNA expression patterns of certain genes related to various diseases; semiquantitative determination of abundance of specific different RNA molecules within a cell or tissue as a measure of gene expression; and cloning of eukaryotic genes in prokaryotes.

U.S. Patent Application Publication No. 2014/0113299 describes a mutant polymerase having a D732N mutation "used in combination with an enzyme having reverse transcriptase activity in a real-time reverse transcriptase (RT) PCR amplification of an RNA target." But U.S. Patent Application Publication No. 2014/0113299 does not describe an RT-PCR reaction that includes a mutant polymerase described herein but does not require or does not include a separate enzyme having reverse transcriptase activity.

LAMP.

As another example, a mutant polymerase described herein can be used to catalyze loop-mediated isothermal amplification (LAMP) of a DNA target. In contrast to PCR in which the reaction is carried out with a series of alternating temperature steps or cycles, isothermal amplification is carried out at a constant temperature, and does not require a thermal cycler. Bst large fragment DNA polymerase is often used for LAMP but denatures at 65-70° C. and therefore cannot catalyze PCR. Although full-length, wild-type Taq (SEQ ID NO: 1) can strand-displace to some extent, its 5'-endonuclease (flap endonuclease, FEN) cleaves the displaced strand so much that it is not appropriate for LAMP.

In LAMP, a target sequence can be amplified at a constant temperature of about 60-using either two or three sets of primers and a polymerase with high strand displacement activity in addition to a replication (i.e., polymerase) activity (e.g., Bst large fragment DNA polymerase). As described herein, a mutant polypeptide having DNA polymerase activity and strand displacement activity can be used for LAMP, in place of or in addition to the relatively sensitive Bst polymerase.

Conventionally, four different primers can used to identify six distinct regions on a target gene, which can increase specificity. An additional pair of "loop primers" can further accelerate the conventional LAMP reaction. Due to the specific nature of the action of these primers, the amount of DNA produced in LAMP can be considerably higher than PCR based amplification. LAMP primer design can be according to well known processes in the art. Except as otherwise noted herein, therefore, the process of the present disclosure can be carried out in accordance with known LAMP protocols.

The product of LAMP can be a series of concatemers of the target region, giving rise to a characteristic "ladder" or banding pattern on a gel, rather than a single band as with PCR. Detection of a LAMP amplification product can be determined according to well known processes in the art. Except as otherwise noted herein, therefore, the process of the present disclosure can be carried out in accordance with such processes. For example, detection of a LAMP amplification product can be determined using photometry for turbidity caused by an increasing quantity of magnesium pyrophosphate precipitate in solution as a byproduct of amplification. This can allow visualization by the naked eye, especially for larger reaction volumes, or via simple detection approaches for smaller volumes. As another example, the reaction can be followed in real-time by measuring the turbidity or by fluorescence using an intercalating dyes (e.g., SYTO 9, SYBR green, Eva Green) can be used to create a visible color change, which can be visually detected or measured by instrumentation. LAMP can be quantitative because dye molecules intercalate or directly label the DNA, and in turn can be correlated to the number of copies initially present. As another example, in-tube detection of DNA amplification can use manganese loaded calcein which starts fluorescing upon complexation of manganese by pyrophosphate during in vitro DNA synthesis.

RT-LAMP.

As another example, a mutant polymerase described herein can be used to catalyze loop-mediated isothermal amplification using RNA template (RT-LAMP). Conventional RT-LAMP requires primers, a reverse transcriptase enzyme, and a DNA polymerase enzyme having strand displacement activity for the amplification of RNA. Similar to RT-PCR, conventional RT-LAMP requires a reverse transcriptase enzyme (not necessary according to methods and mutant polymerases described herein) to synthesize complementary DNA (cDNA) from RNA sequences. This cDNA can then be amplified using DNA polymerase. As described herein, use of a mutant polymerase can eliminate the need for a separate reverse transcriptase enzyme is not required.

RT-LAMP can be desirable because of the relatively low reaction temperature and no need for thermocycling equipment necessary for other methods like PCR.

In conventional LAMP, four specially designed primers can recognize distinct target sequences on a template strand. Such primers bind only to these sequences which allows for high specificity. Out of the four primers involved, two of them are "inner primers" (FIP and BIP), designed to synthesize new DNA strands. The outer primers (F3 and B3) anneal to the template strand and also generate new DNA. These primers are accompanied by a DNA polymerase which can aid strand displacement and can release the newly formed DNA strands.

The BIP primer (in conventional methods, accompanied by a reverse transcriptase enzyme, which is not required with mutant polymerases described herein), can initiate the process by binding to a target sequence on the 3' end of an RNA template and synthesizing a copy DNA strand. The B3 primer can also bind the 3' end and along with a polypeptide having DNA polymerase activity (e.g., a mutant polymerase described herein) can simultaneously create a new cDNA strand while displacing the previously made copy. The double stranded DNA containing the template strand is no longer needed.

At this point, the single stranded copy can loop at the 3' end as it binds to itself. The FIP primer can bind to the 5' end of this single strand and accompanied by a polypeptide having DNA polymerase activity (e.g. a mutant polymerase described herein), can synthesize a complementary strand. The F3 primer, with DNA polymerase, can bind to this end and can generate a new double stranded DNA molecule while displacing the previously made single strand.

This newly displaced single strand can act as the starting point for a LAMP cycling amplification. The DNA can have a dumbbell-like structure as the ends fold in and self anneal. This structure can become a stem-loop when the FIP or BIP primer once again initiates DNA synthesis at one of the target sequence locations. This cycle can be started from either the forward or backward side of the strand using an appropriate primer. Once this cycle has begun, the strand can undergo self-primed DNA synthesis during the elongation stage of the amplification process. As described above, this amplification can take place in about an hour, under isothermal conditions between about 60-65° C.

A mutant polymerase described herein can be used in RT-LAMP and not require the presence of a separate reverse transcriptase enzyme. In some embodiments, a mutant polymerase described herein is used in RT-LAMP and a separate reverse transcriptase enzyme is not present in the reaction mixture.

It has also been discovered that a Bst large fragment DNA polymerase comprises reverse transcriptase activity. In some embodiments, RT-LAMP can be performed with a Bst large fragment DNA polymerase (e.g., Manta or Bst 2.0 from Enzymatics, Bst 1.0 from New England Biolabs). In some embodiments, a Bst large fragment DNA polymerase (e.g., Manta or Bst 2.0 from Enzymatics, Bst 1.0 from New England Biolabs) is used in RT-LAMP and a separate reverse transcriptase enzyme is not present in the reaction mixture. In some embodiments, a Bst large fragment DNA polymerase comprising a sequence of SEQ ID NO: 10, or a variant at least 95% identical thereto having DNA polymerase activity, reverse transcriptase activity, and strand displacement activity, is used in RT-LAMP and a separate reverse transcriptase enzyme is not present in the reaction mixture. In some embodiments, a RT-LAMP reaction mixture includes both a mutant polymerase disclosed herein and a Bst large fragment DNA polymerase (e.g., (Manta or Bst 2.0 from Enzymatics, Bst 1.0 from New England Biolabs) (e.g., a Bst large fragment DNA polymerase having a sequence of SEQ ID NO: 10, or a variant at least 95% identical thereto having DNA polymerase activity, reverse transcriptase activity, and strand displacement activity).

Thus, methods and compositions described herein can be applied to improve the nucleic acid detection in RT-PCR, LAMP, or RT-LAMP. Both RT-PCR and RT-LAMP can benefit from high temperature tissue and virus disruption, and higher temperature reaction, to improve the convenience and selectivity of RNA detection, such as for Ebola and Dengue. A mutant polymerase described herein can allow such higher temperatures and remove the requirement for a separate RT enzyme in the reaction.

The buffer for use in the various PCR assay mixtures described herein is generally a physiologically compatible buffer that is compatible with the function of enzyme activities and enables cells or biological macromolecules to retain their normal physiological and biochemical functions. Typically, a physiologically compatible buffer will include a buffering agent (e.g., TRIS, MES, $PO_4$, HEPES, etc.), a chelating agent (e.g., EDTA, EGTA, or the like), a salt (e.g., ammonium sulfate, NaCl, KCl, $MgCl_2$, $CaCl_2$, NaOAc, KOAc, $Mg(OAc)_2$, etc.) and optionally a stabilizing agent (e.g., sucrose, glycerine, TWEEN™ 20, etc.).

Various PCR additives and enhancers can be employed with the methods described herein. For example, betaine (e.g., MasterAmp™ 10× PCR, Epicentre Biotechnologies) can be added to the PCR assay. Betaine can be included at final concentration about 0.75 M to about 2 M.

As another example, a mutant polymerase described herein can be used in conjunction with a PCR enhancer described in US Pat Pub No. 2012/0028259 or WO 2012/088479, each incorporated herein by reference. For example, a mutant polymerase can be used in conjunction with a PCR enhancer including trehalose (e.g., about 0.1 to about 1.0 M D-(+)-trehalose per amplification reaction mixture volume), carnitine (about 0.1 to about 1.5 M L-carnitine per amplification reaction mixture volume), or a non-ionic detergent (e.g., NP-40, IGEPAL® CA-630, BRIJ™-58, TWEEN™-20, or TRITON™ X-100 at about 0.01% to about 8% non-ionic detergent per amplification reaction mixture volume) or optionally one or more of heparin (e.g., an amount of heparin equivalent to about 2 units to about 50 units heparin per mL of whole blood, plasma, or serum in an amplification reaction mixture), casein (at least about 0.05% up to about 2.5% per amplification reaction mixture volume), or polyvinylpyrrolidone (PVP) or a modified polymer of PVP (PVPP) (e.g., about 0.1% up to about 25%). As another example, a mutant polymerase can be used in conjunction with a PCR enhancer including about 0.6 M trehalose per amplification reaction mixture volume; about 0.5 M carnitine per amplification reaction mixture volume; or a non-ionic detergent (e.g., a polyoxyethylene cetyl ether at about 0.04% to about 0.2% or a nonyl phenoxylpolyethoxylethanol at about 0.4% to about 0.8% per amplification reaction mixture volume); or optional heparin at about 10 units per mL of whole blood, blood fraction, plasma, or serum.

As another example, a mutant polymerase described herein can be used in conjunction with commercially available PCR amplification reaction enhancers, such as MasterAmp™ 10× PCR Enhancer, Epicentre Biotechnologies; TaqMaster PCR Enhancer, MasterTaq Kit, PCR Extender System, 5 PRIME GmbH; Hi-Spec Additive, Bioline; PCRboost™, Biomatrica®; PCRX Enhancer System, Invitrogen; Taq Extender™ PCR Additive, Perfect Match® PCR Enhancer, Stratagene; Polymer-Aide PCR Enhancer, Sigma-Aldrich.

Chemistry and Molecular Engineering

The following definitions and methods are provided to better define the present disclosure and to guide those of ordinary skill in the art in the practice of the present disclosure. Unless otherwise noted, terms are to be understood according to conventional usage by those of ordinary skill in the relevant art.

A chemical bond is understood as an attraction between atoms of a biomolecule and atoms of a matrix material that allows the formation of a linkage between atoms (e.g., atoms of the same molecule or different molecules). A bond can be caused by an electrostatic force of attraction between opposite charges, either between electrons and nuclei, or as the result of a dipole attraction. A bond can be, for example, a covalent bond, a coordinate covalent bond, an ionic bond, polar covalent, a dipole-dipole interaction, a London dispersion force, a cation-pi interaction, or hydrogen bonding.

Compositions and methods described herein utilizing molecular biology protocols can be according to a variety of standard techniques known to the art (see, e.g., Sambrook and Russell (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russell (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

A mutation refers to a change introduced into a parental sequence, including, but not limited to, substitutions, insertions, or deletions (including truncations). The consequences of a mutation include, but are not limited to, the creation of a new character, property, function, phenotype or trait not found in the protein encoded by the parental sequence.

Enzyme activity refers to the specificity and efficiency of a DNA polymerase. Enzyme activity of a DNA polymerase can also be referred to as polymerase activity, which typically refers to the activity of a DNA polymerase in catalyzing the template-directed synthesis of a polynucleotide. Enzyme activity of a polymerase can be measured using various techniques and methods known in the art. For example, serial dilutions of polymerase can be prepared in dilution buffer. The reaction mixtures can be incubated at, e.g., 74° C. and stopped by cooling to, e.g., 40° C. and adding ice-cold EDTA. An aliquot can be removed from each reaction mixture. Unincorporated radioactively labeled dCTP can be removed from each aliquot by gel filtration (e.g., Centri-Sep, Princeton Separations, Adelphia, N. J.). The column eluate can be mixed with scintillation fluid. Radioactivity in the column eluate can be quantified with a scintillation counter to determine the amount of product synthesized by the polymerase. One unit of polymerase activity can be defined as the amount of polymerase necessary to synthesize 10 nmole of product in 30 minutes (see e.g., Lawyer et al. 1989 J. Biol. Chem. 264, 6427-647). Other methods of measuring polymerase activity are known in the art (see e.g. Sambrook and Russell (2001) Molecular Cloning: A Laboratory Manual, 3d ed., Cold Spring Harbor Laboratory Press, ISBN-10: 0879695773).

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Green and Sambrook 2012 Molecular Cloning: A Laboratory Manual, 4th ed., Cold Spring Harbor Laboratory Press, ISBN-10: 1605500569; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide or polypeptide variants having, for example, at least 95-99% identity to the reference sequence described herein and screen such for desired phenotypes according to methods routine in the art.

Nucleotide or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6× SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6× SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$=81.5° C.+16.6($\log_{10}$ [$Na^+$])+0.41(fraction G/C content)−0.63(% formamide)−(600/l). Furthermore, the $T_m$ of a DNA:DNA hybrid is decreased by 1-1.5° C. for every 1% decrease in nucleotide identity (see e.g., Sambrook and Russell, 2006).

Host cells can be transformed using a variety of standard techniques known to the art (see, e.g., Sambrook and Russell (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Green and Sambrook 2012 Molecular Cloning: A Laboratory Manual, 4th ed., Cold Spring Harbor Laboratory Press, ISBN-10: 1605500569; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to a mutant polymerase described herein or a nucleic acid encoding such mutant polymerase or, optionally, a primer, a buffer, or other composition or component (e.g., a magnesium salt) necessary or helpful for PCR. Such packaging of the components separately can, if desired, be presented in a pack or dispenser device which may contain one or more assay unit forms containing a composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has,"

"having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

This study showed the isolation of mutants resistant to inhibitors of food assays thus eliminating or decreasing the time and extent of these extraction procedures or improve the reliability of PCR assays of food. Total *E. coli* cells were used as a source of enzyme to screen circa 4,000 mutagenized clones that expressed Taq DNA polymerase from a plasmid. The screen used crude extract as the enzyme and template. Expression of 50 µl cultures in 96-well plates was induced, and PCR primers for endogenous ribosomal DNA (385 bp product) (forward TACAGACGTT-TAAGCTTCGCAATTACC GGTT (SEQ ID NO: 11) and reverse AAAAAGCTGCAAATTGCGGTAGGTATTATT (SEQ ID NO: 12)), reaction buffer and SYBR Green were added as 35 µl directly to 3-5 µl of the bacterial culture, followed by immediate temperature cycling. Wild-type Taq or Klentaq1 clones give rise to robust PCR amplification under these conditions. When chocolate or cracked-pepper extract (3 µl of 10% w/v) was also included, PCR was suppressed for all but a few clones. At a frequency of about 1% in this mutagenized library, real-time PCR analysis identified enzyme variants that could still catalyze PCR in the presence of inhibitors. The cracked pepper screen gave rise to clone A111 (FIG. 20) and subsequent DNA sequencing showed only a single change, D732N. Resistance to chocolate, blood, and bile was subsequently observed for enzyme A111.

Cycling conditions: Pre-heat: both 10'/95° C. and 5'/95° C. work, followed by 30 sec/95° C., 40 sec/54° C. and 3 min/70° C., for 40-42 cycles. Melting curve analysis in the interval 60-90° C. followed the amplification.

Cycler used: Opticon-2, BioRad. Reactions contained 0.6×SYBR Green, and 2-3 µl 10% black pepper extract per 35 µl reaction volume.

The target for these inhibition tests is in the human cross-link repair 1A gene. Human DNA was supplied at 10 ng per 50 µl reaction volume in the no-inhibitor controls and the food reactions. No exogenous template DNA was added to the blood reactions. The amplicon size is 976 bp, and the primers sequences are For: ctaccaaggtaatgaagcaaatggatat (SEQ ID NO: 13); Rev: tggcagcaaccaaagtatatgaaaggg (SEQ ID NO: 14). Taq 732N enzyme stock concentration was 0.8 OD280, and the amount used varied as described. Taq WT was supplied by NE Biolabs and used at 0.8 µl per reaction. PCR reaction buffer used at 1× was diluted from 10× stock 500 mM Tris-CI, pH 9.1, 160 mM ammonium sulfate, 0.25% Brij 58, and 25 mM magnesium chloride. The PCR cycling program was 94° C. 10 minutes once; 35 cycles of 94° C. 40 second, 60° C. 1 minute, 70° C. 3 min.

Bar chocolate (Lindt, 70% cocoa) was suspended at 10% w/v in water using a bead-beater and clarified by centrifugation. The supernate was then diluted with reaction mix to final amounts per 50 µl reaction of 0, 0.15, 0.3, 0.6, and 1.2 µl, increasing left to right, as indicated. Taq D732N enzyme used was only 0.04 µl for the zero inhibitor control, since it was found to cause smearing at this pH if more was used. When inhibitor was present, 0.8 µl of Taq D732N was used. Wild-type Taq (NE Biolabs) was included at 0.8 µl per each reaction. FIG. 17 shows that Taq D732N produced results at all but the highest amount of chocolate.

Black pepper (Shoppers Value, supermarket) was suspended at 10% w/v in water and was filtered to remove solids. Tested volumes added to the PCR reactions were 0, 0.063, 0.125, 0.25, 0.5 µl. Whole blood (single-donor Valley Biomedical, Virginia, USA.) was stored frozen. Thawed amounts added to the PCR reactions were 0, 5%, 10%, 15%, 20% of the reaction volume. FIG. 18 shows that Taq D732N produced results with the first two concentrations of black pepper, and all tested concentrations of whole blood.

Example 2

Half-Dumbbell Construction.

A DNA "handle" was amplified from phage lambda DNA by PCR using primers 13.16 (GGCATTGTTTGGTAGGT-GAGAGATCT (SEQ ID NO: 15)) and 13.17' (ACAAATGACAAGAGTCTGGTTCAGAAGATA (SEQ ID NO: 16)), precipitated with PEG+SDS, and digested with HindIII and BglII at its opposite ends. A stem loop consisting of self-annealed, 5'-phosphorylated DNA 11.164 (5P- agctCTGTCTCTTATACACATCTaataGTTTAACTTTAA-GAAGGAGATATAaataAGAT GT GTATAAGAGACAG (SEQ ID NO: 17)) was formed using T3 ligase (Enzymatics) in T4 ligase buffer (NEB) supplemented with 11 mM NaCl. This product was precipitated with PEG+SDS and resuspended in 1× Cutsmart buffer (NEB). To each 1.5 µg of DNA was added 1 µl T7 exonuclease (NEB) on and incubated on ice for 40 minutes to allow removal of ca. 50 bases from the 5'-BgIII end, followed by heat denaturation of the exonuclease at 75° C. for 15 min. In a buffer of TEN+200 mM NaCl, primer 13.16 was annealed to replace some of the bases removed by the T7 exonuclease, with a gap in "front" of it at its 3'-end. Klentaq1 is not able to synthesize any noticeable bases at this gap, but Bst DNA polymerase large fragment (Manta from Enzymatics) can extend this 1.2 kb DNA product to 2.4 kb by strand-displacement, and then copying the displaced strand. Compared to the parent (full-length) Taq or Klentaq1 enzymes, mutants D732N of each show a significant ability to produce the 2.4 kb product (FIG. 6B).

RT-LAMP MS2 RNA Primer Mixture.

RT-LAMP MS2 RNA primer mixture (TGTCATGG-GATCCGGATGTT (SEQ ID NO: 18), CAATAGAGCCGCTCTCAGAG (SEQ ID NO: 19), CCAGAGAGGAGGTTG CCAA (SEQ ID NO: 20), TGCAGGATGCAGCGCCTTA (SEQ ID NO: 21), GCC-CAAA CAACGACGATCGGTAgagtcAAACCAG-CATCCGTAGCCT (SEQ ID NO: 22), and GCACGTTCTCCAACGGTGCTgagtcGGTTGCTTGTTC-AGCGAACT (SEQ ID NO: 23)) contained 120 µl of 1.05× complete reaction buffer (see below), 20 µl of F3 and B3 from 10 µM in each stock, and 20 µl of Fip, Bip, FL and BL from 40 µM in each stock (i.e., ratios 1:4:4), and 1 µl of Antarctic UDG (NE biolabs). Four µl was added to 21-22 µl of otherwise complete reaction volume as a hanging drop hot start (see below).

RT-Lamp Reactions.

RT-LAMP reactions used 7 times less dNTP, and half as much primer, compared to many published LAMP reactions (see e.g., Tomita et al. 2008 Nature Protocols 3, 877-882; Tanner et al. 2012 Biotechniques 53, 81-89; Chander et al. 2014 Frontiers in Microbiology, 5). KLA buffer (1×=50 mM Tris-HCl pH 8.55, 2.9 mM MgCl$_2$, 0.025% Brij 58, 8 mM ammonium sulfate) was supplemented with final 0.75 M betaine, 0 or 25 mM KCl, 4 mM DTT, 0.1 mM CaCl$_2$ and 200 µM each of 5 dNTP (A,G,C,T,U). The DTT was included to allow for efficient thermal inactivation of E. coli RNase I. The fifth triphosphate, dUTP, was included to allow the potential use of uracil glycosylase (UDG) to allow removal of contaminating product from previous amplifications, but no UDG was used here except in the primer mix (see above). Instead calcium-requiring DNase I (NE Biolabs) was used as follows: At time of LAMP reaction setup, the pre-reaction mix at 1.05× and lacking enzyme and nucleic acid, was supplemented with 1/100 volume of pancreatic DNAse I stock (NE Biolabs; final 10 µg/ml DNAse, 0.1 mM CaCl$_2$) to combat carry-over DNA contamination. The subject DNA polymerase enzyme (about 0.5 to 1 µg or as indicated) to each 21 µl and incubated at room temperature for 5-10 minutes, during which 4 µl of primer mixture were dispensed to the inside of each test tube cap, for the hanging-drop hot start. Eva Green dye (final 1 µl of 20×; Life Technologies) was included in the 21 µl or added to the primer mix. After a further 10 minutes at room temperature, reactions were allowed to equilibrate in the hot block of a thermal cycler at 73° C. for 30 seconds to inactivate DNase.

Hanging Drop Hot Start: The cycler program was then paused. Within a minute, each tube or 8-mer of tubes was given a brisk downward shake to add the primers to the reaction, another downward shake, and returned to 68° C. If electrophoresis was used, 1.7 µl was loaded onto 1.2% agarose gels. Control reactions showed that DNAse I is inactivated in 30 seconds if kept warm thereafter, yet 10-15 seconds of DNase at room-temperature in contact with the primers was sufficient to prevent the LAMP reaction. MS2 RNA was diluted to 2-3 ng/µl in 0.1×LAMP reaction buffer, and added to reactions as 1 µl.

RNase I Treatment.

RNase I treatment, when used, was carried out in 0.1-strength RT-LAMP reaction buffer, at 2 or 3 ng MS2 RNA per µl in a volume of 25 µl, with or without 0.2 units of E. coli RNase I (Epicentre). Incubation was at ambient temperature for 10 minutes, before addition of LAMP reaction mix containing DNAse I as described above. 1 µl (2-3 ng RNA) was thus included in 26 µl reactions.

Results.

RT-LAMP with full-length Taq-D732N and 5'-exo mutations D119A and D119N showed improved clarity (see e.g., FIG. 19). Improved clarity of the banding pattern, as usually observed for standard LAMP using Bst DNA polymerase, is apparent if an additional mutation near the metal-binding site of the 5'-exonuclease a.k.a. 5'-flap endonuclease is employed (see e.g., FIG. 19). D142A failed to have this effect. First column is D119D, i.e. wild-type at codon 119. All lanes used D732N Taq.

Example 3

The following example demonstrates strand displacement activity of full length mutant polymerase A111 (SEQ ID NO: 3). Methods are according to Example 2 unless otherwise described.

Figure 1:
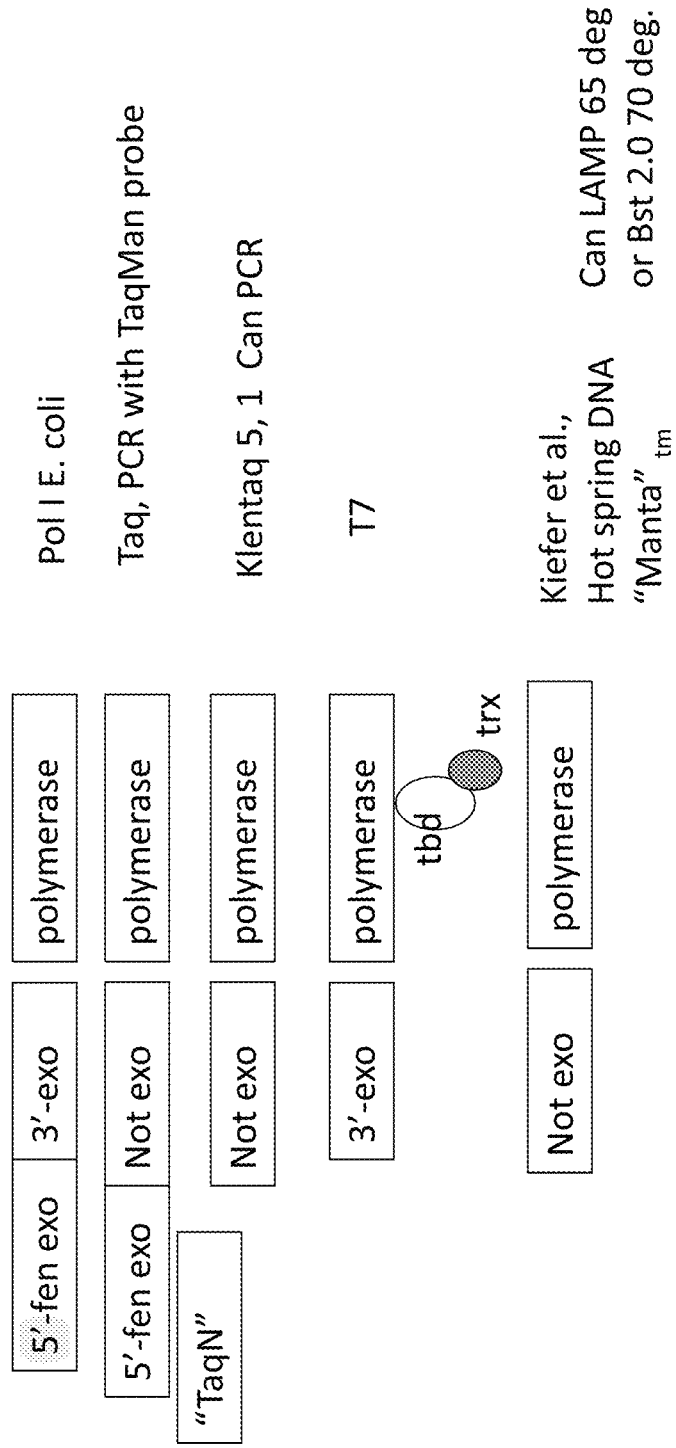
FIG. 1 is a diagram showing phenotypes of a variety of polymerases. The hot spring DNA polymerase called Bst large fragment, Bst 2.0, is available commercially ("Manta", NE Biolabs). While Bst large fragment is very similar to Klentaq1, it cannot stand more than 65° C. (70° C. for Bst 2.0) so it cannot do PCR, which requires thermostability to 95° C. The crystal structures of Klentaq1 and Bst large fragment are very similar, and they are 50% homologous by amino acid sequence. Full-length Taq has an N-terminal domain that cuts displaced DNA ("flaps") ahead of it.
Figure 2:
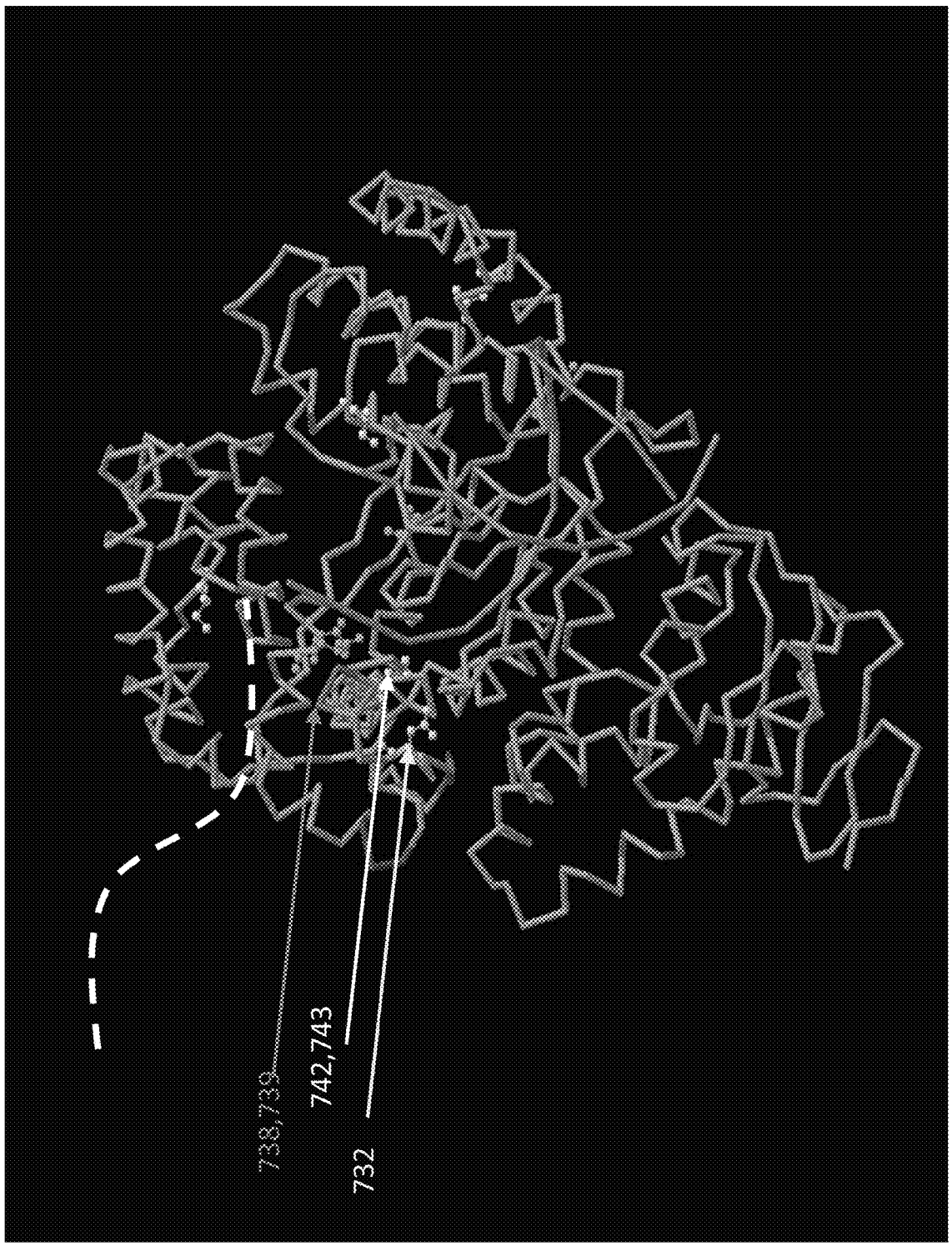
FIG. 2 shows a crystal structure of Klentaq1. Incoming DNA template takes a sharp turn as it enters the enzyme to be copied (shown approximately by the dotted line). This is more clearly visible on the crystal structure of Bst DNA polymerase. Numbering is from wild-type, full-length Taq. Amino acids 742,743 are adjacent to the template strand, and several mutations here have been described (see e.g., Yamagami et al. 2014 Front Microbiol 5:461). But amino acid 732 is not near DNA in the crystal structure. Also indicated are indicated amino acids 738,739, where inserts can be placed while retaining activity. Other insert positions are disclosed in Yamagami et al. 2014 Front Microbiol 5:461.
Figure 3:
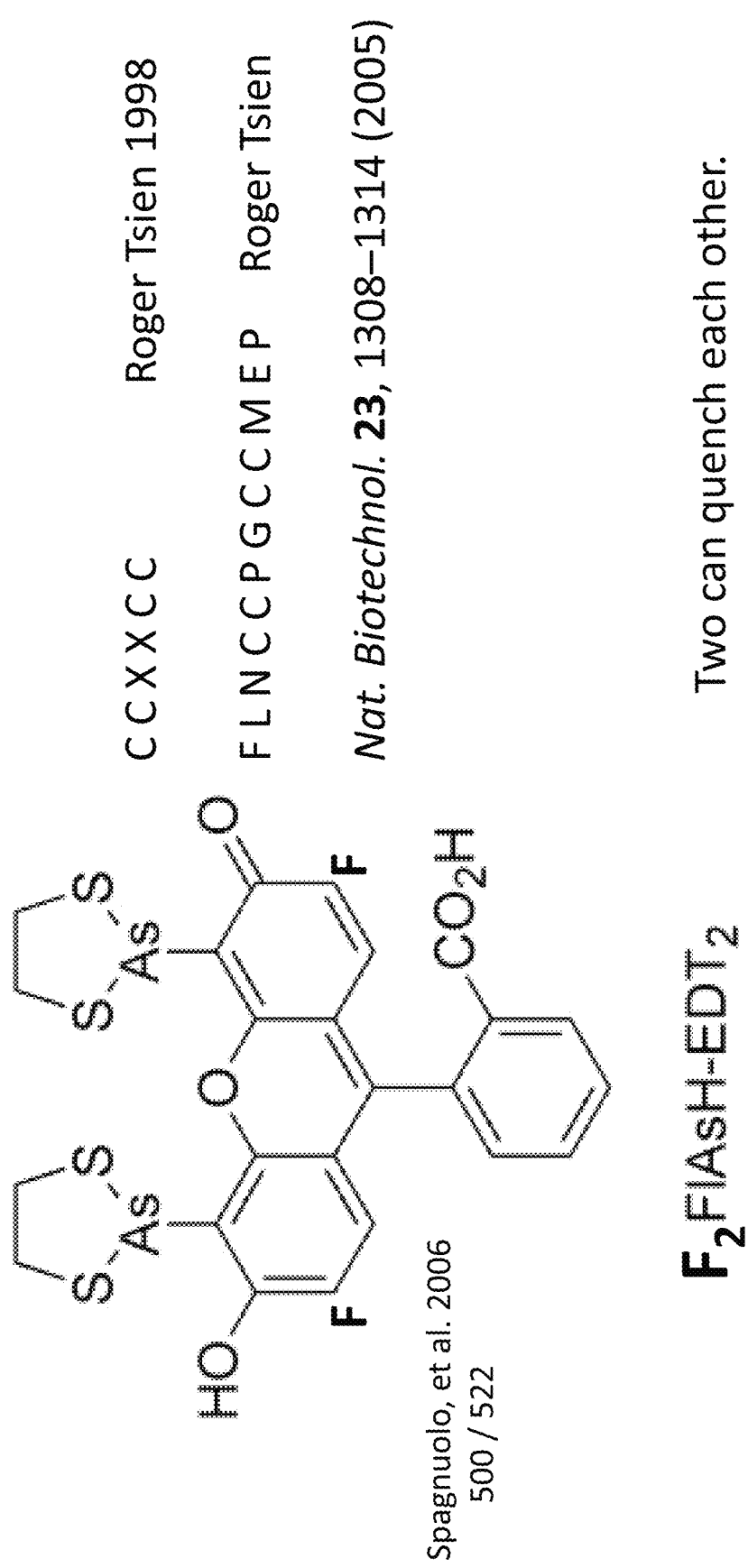
FIG. 3 is a diagram showing F1AsH, a label that attaches only to CCXXCC at the double cysteines (see e.g., Tsien 2005 Nat Biotechnol 23, 1308-1314). A preferred sequence can be FLNCCPGCCMEP. Several versions of F1AsH were inserted between 738,739 (per wild type Taq numbering) of Klentaq1, as further described herein.
Figure 5:
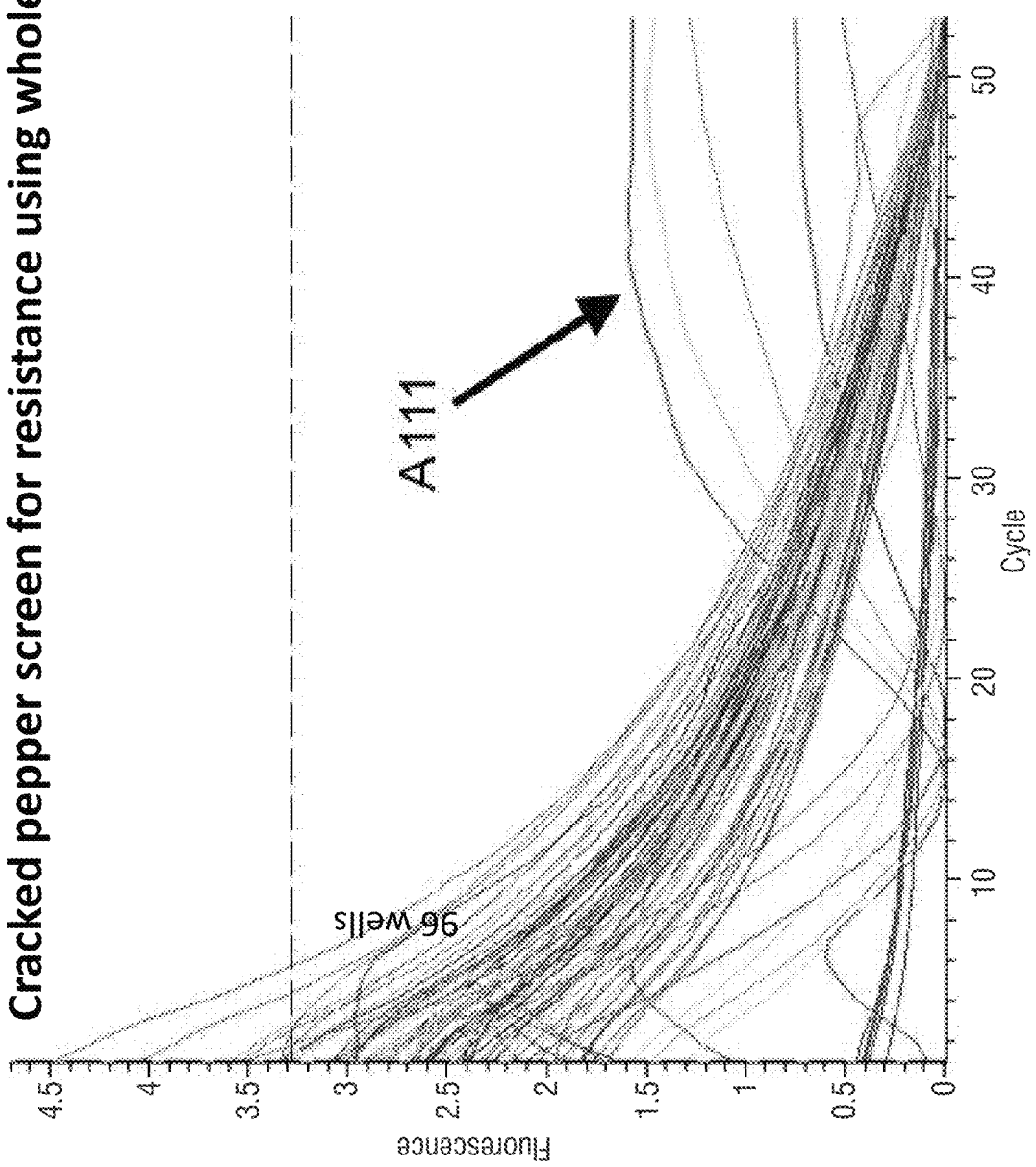
FIG. 5 shows real time PCR results from a cracked pepper screening assay for resistance using whole *E. coli* as PCR enzyme. Presented is raw data of 96 curves of SyBr Green fluorescence. Rising curves from cycle 20-40 represent successful PC or 4 less-resistant controls. Five µl of water extract of black pepper was included in each reaction. The highest rising curve was Taq DNA polymerase clone A111 (SEQ ID NO: 3), with a single mutation D732N. Resistance to chocolate, blood and bile was subsequently observed for enzyme A111.

Mutant polymerase A111 (SEQ ID NO: 3) was originally identified as resistant to inhibitors of PCR assays of food (see U.S. Patent Application Publication No. 2014/0113299, published 24 Apr. 2014). From a mutagenized library, real-time PCR analysis identified enzyme variants that could still catalyze PCR in the presence of inhibitors. Clone A111 was identified from assays with cracked pepper inhibitor (see e.g., FIG. 5) and subsequent DNA sequencing (SEQ ID NO: 3) showed only a single change, D732N, from wild type Taq (SEQ ID NO: 1).

Strand-displacement activity (as in Bst polymerase) was attempted to be engineered into Klentaq1 (SEQ ID NO: 2) without compromising its thermostability, by swapping sections of these two aligned sequences, or by inserting a DNA binding domain between K738 and S739. Such efforts were not successful due to loss of thermostability sufficient for PCR.

Strand Displacement Activity

Figure 6:
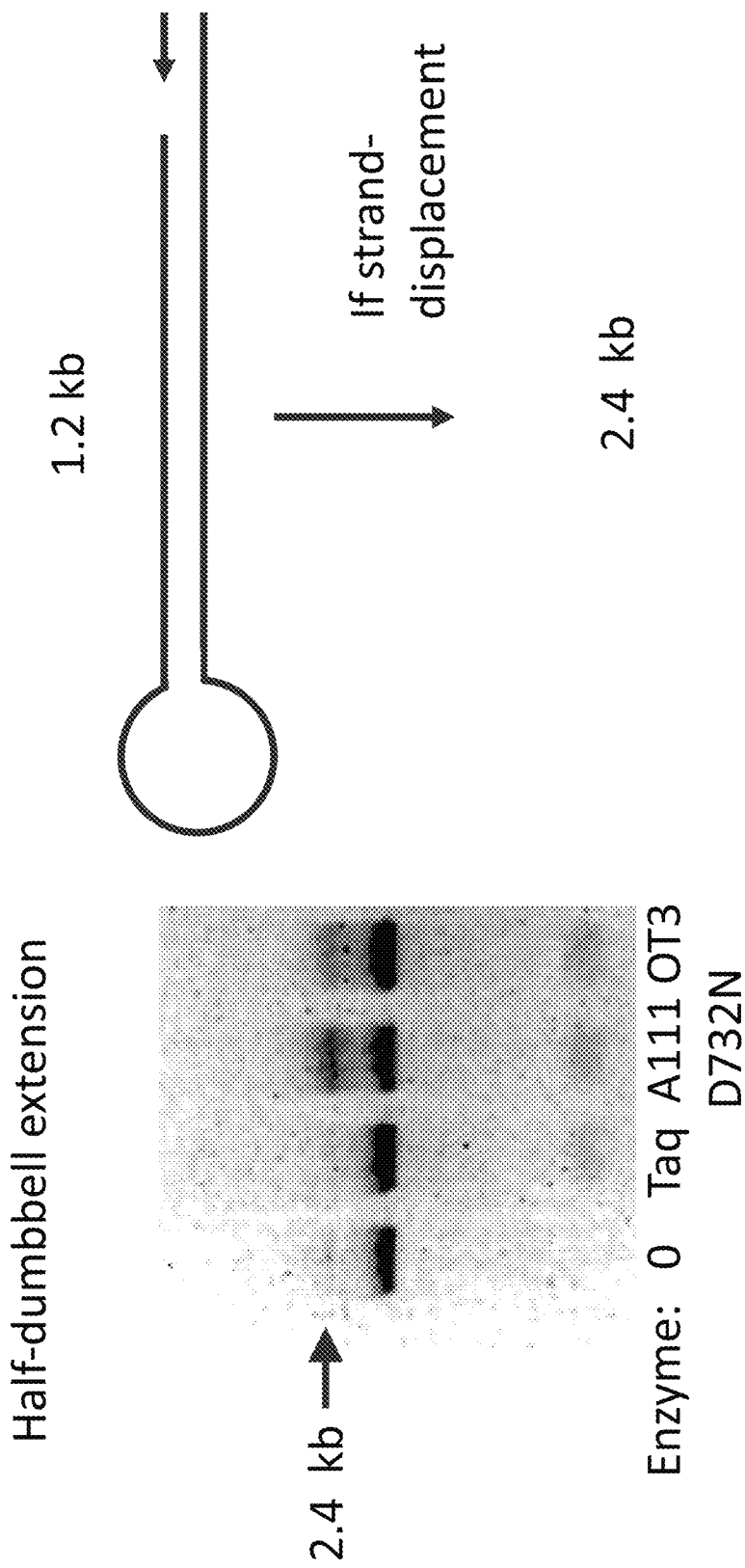
FIG. 6 shows a strand-displacement half-dumbbell test. This assay tested whether an enzyme could displace 1.2 kb, go around a loop, and come back to an end, producing a predicted, discrete 2.4 kb band.
Figure 7:
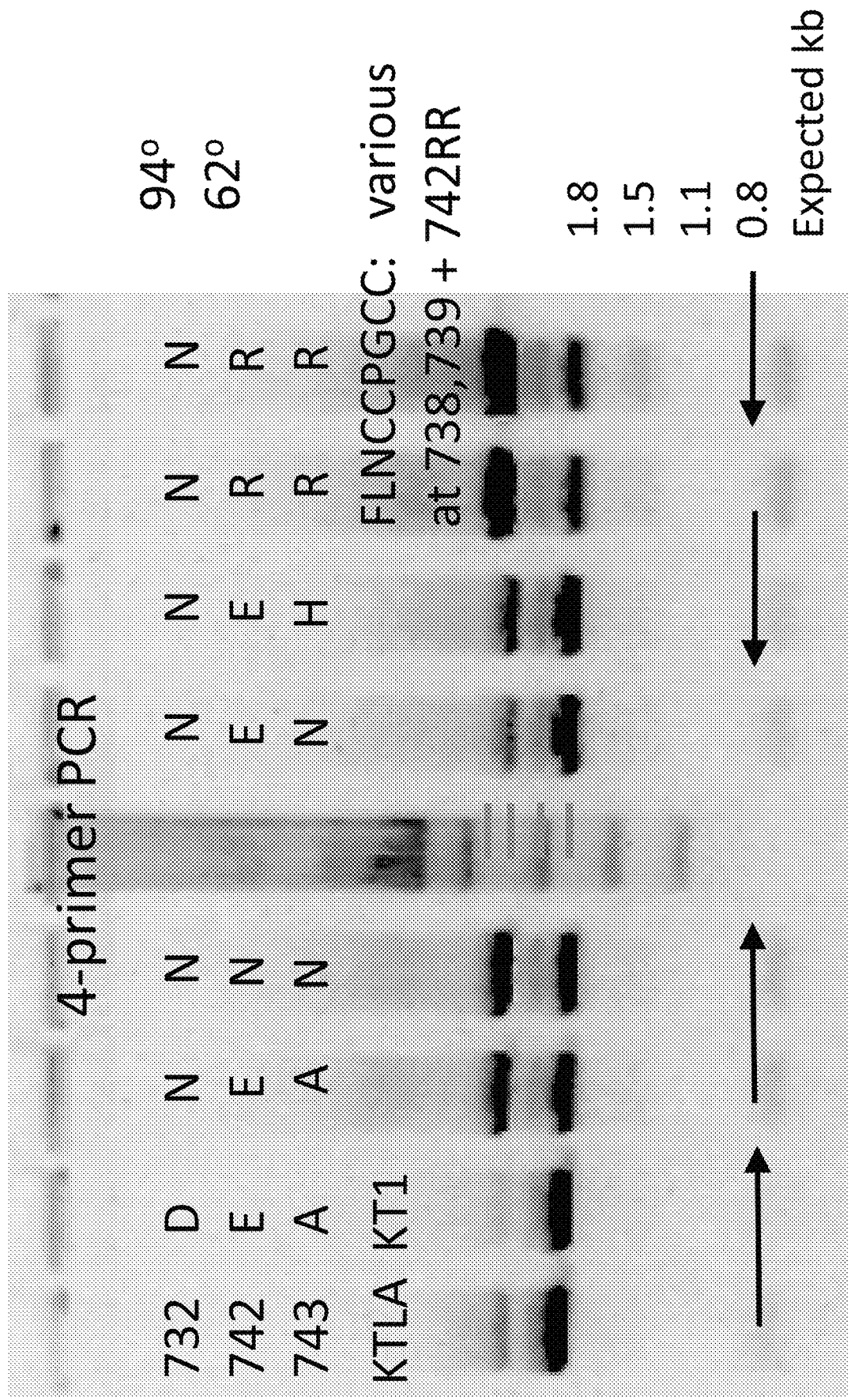
FIG. 7 shows four-primer PCR as a test to compare mutant polymerases. It was thought that Klentaq1 (SEQ ID NO: 2) could PCR-amplify only the inner-primed product, since it cannot start at the outer-nested primers and displace the inner primed DNA that is already there. D732N can do some larger product. The largest expected product is not made by any of the enzymes depicted in FIG. 7.

Mutant polymerase A111 (SEQ ID NO: 3) was tested in a strand-displacement half-dumbbell test (see e.g., FIG. 6). This assay tested whether an enzyme could displace 1.2 kb, go around a loop, and come back to an end, producing a predicted, discrete 2.4 kb band. As shown in FIG. 6, mutant A111, i.e., TaqD732N (SEQ ID NO: 3) did surprisingly well in this assay. This assay was designed so that strand-displacement would cause a band at 2.4 kb, rather than a smear with other assays. But in a full length Taq mutant, the 5'-flap would chew away displaced strand, so a D732N mutation in Klentaq1 (truncated A111, or KT-A111) (SEQ ID NO: 4) was studied.

Reverse Transcriptase Activity.

Another goal was to combine inhibitor-resistant mutations of Taq or Klentaq1 with significant reverse transcriptase (RT)-active mutations different than four already described (see e.g., Blotter et al. 2013 Angewandte Chemie International Edition 52, 11935-11939; Ong et al. 2006 Journal of Molecular Biology 361, 537-550).

Surprisingly, it was discovered that mutant polymerase A111 i.e., TaqD732N (SEQ ID NO: 3) showed some RT-PCR activity (FIG. 20). Two MS2 phage RNA targets, E and L, 210 bp each (MS2-E-FOR: AGGGTGCATAT-GAGATGCTTAC (SEQ ID NO: 24), MS2-E-REV: AGA-TACCTAGAGACGACAACCA (SEQ ID NO: 25), MS2-L-FOR: GATCGTATCCGCTCACACTAC (SEQ ID NO: 26), MS2-L-REV: TGCAATCTCACTGGGACATATAA (SEQ ID NO: 27), were amplified from 4 pg phage RNA with 0.25, 0.125 and 0.06 µl D732N mutant enzyme, or 0.5, 0.25 and 0.125 µl wild-type Taq (NEB) (lanes 1-3 each enzyme) in 35 µl reactions for 32 PCR cycles. Control reactions (lanes 4-6) contained no RNA. An RT-step of 30 min at 68° C. preceded the PCR amplification. 10 µl of amplified products were run in a 2.5% agarose gel, stained with ethidium bromide, along with a 100 bp DNA ladder (lanes M). Reaction buffer was (1×) 50 mM Tris-HCl, pH 9.1, 16 mM AmSO$_4$, 2.5 mM MgCl$_2$, 0.025% Brij-58, 200 µM each dNTP. Each 35 µl reaction was also supplemented with 1/10 volume of PCR Enhancer Cocktail 1 (DNA Polymerase Technology). RT+Cycling conditions (one-tube RT-PCR): RT step 2 min/ 75° C., 2 min/54° C., 30 min/68° C., PCR cycling 2 min/95° C. followed by 32 cycles 25 sec/95° C., 40 sec/54° C., 1 min/70° C.

This observation prompted generation of a Klentaq1-D732N enzyme (SEQ ID NO: 4) for LAMP with RNA template (RT-LAMP).

TABLE 1

Polymerase Mutations

| Klentaq1 mutant | Codon 732 change | 738,739 insert | Codons 742,743 |
|---|---|---|---|
| KT732N | D732N | NONE | EA wild-type |
| KTflnC4RR | D732N | FLNCCPGCC | RR |
| KT-NRR | D732N | NONE | RR |
| KT-DRR | NONE | NONE | RR |

Figure 9:
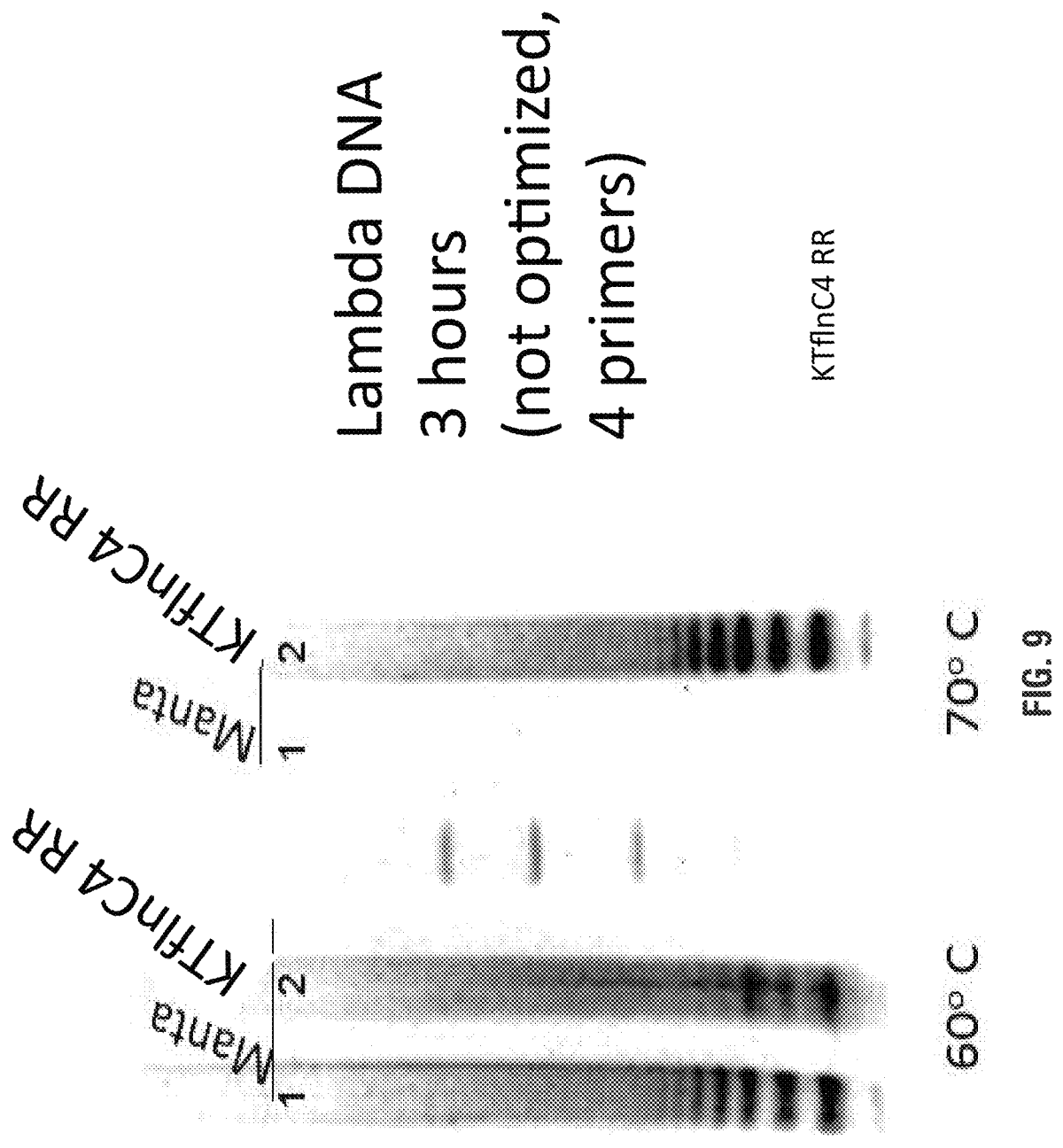

Mutant polymerase was tested in a 4 primer (non-optimized assay; 14.163 LAMP F3 lambda GTAAAAACACCTCACGAGTT (SEQ ID NO: 28), 14.164 LAMP B3 lambda TTTACGAACATTAAGCGACTT (SEQ ID NO: 29), 14.165 FIP LAMP lambda TCCTACGGT-CAAGAGAAGCAATAAA (−) CACCTAAGTTCT-CACCGAAT (SEQ ID NO: 30), 14.166 BIP LAMP CTTTCCACATGCAGGATTTTGG (−) ATGCACGCAAT-GGTGTAG (SEQ ID NO: 31)) for strand displacement activity run at 60° C. and 70° C. Positive control was Manta polymerase (a Bst DNA large fragment polymerase). Mutant polymerase KTflnC4RR (truncated polymerase having D732N; FLNCCPGCC (SEQ ID NO: 32) insert at 738,739; and E742R and A743R (EA742RR)) showed strand displacement activity, notably at 70° C. where Manta was inactivated (see e.g., FIG. 9). KTflnC4RR was found to catalyze LAMP for a lambda DNA target as well as Bst large fragment, after 3 hours.

TaqLamp1 (also named KTflnC4) differs in several ways from wild-type Taq DNA polymerase. 1) The first 278 amino acids are deleted, making it Klentaq1; 2) D732N; 3) E742R and A743R (EA742RR); 4) insertion, between 738 and 739, of FLNCCPGCC.

After elimination all of the other changes, it was shown that D732N catalyzes LAMP. Additional mutant polymerases were tested in RT-LAMP real-time traces using Eva Green indicator. Template was 3 ng of MS2 RNA in 26 µl reactions volumes. On the trace diagrams, inflected curves indicate positive LAMP reactions (see, e.g., FIG. 14A). Curves or flat traces resulted for no-RNA and RNA+RNase (lines having no large circle data points), and their melt-curves showed no product melting near 86° C. (see, e.g., FIG. 14A). Although KT-RR (i.e., KT having both E742R and A743R substitutions, SEQ ID NO: 6) showed the fastest signal, it also had the highest NTC curve (no-template control) and RNase I curves; these negative control products melted at 80° C. or 65° C. As shown in FIG. 14B, genuine LAMP products melted at 85-86.5° C. Parallel experiments without Eva Green usually have LAMP product (DNA ladder on gels) 5-10 minutes sooner than the inflection points shown here.

Control experiments showed that a modified Bst DNA polymerase commercially provided for LAMP, can by itself surprisingly carry out RT-LAMP if MS2 RNA template is supplied without RNase I treatment. Additionally, studies of Bst 1.0 polymerase (New England Biolabs), without any RT (reverse transcriptase) enzyme has been shown to catalyze RT-LAMP using the conditions described herein (see, e.g., lanes 5-8 of FIG. 21).

It was shown that a single mutation to Taq DNA polymerase, D732N, confers a significant level of reverse transcriptase activity and concomitant strand displacement ability. The ability of slightly mutated Taq (only 1 codon) or Klentaq1 (1 or 2 codons) to catalyze LAMP was surprising enough, but for reverse transcriptase activity to be a side-effect was even more surprising. Additionally, the E742R and A743R (EA742RR) mutations and the insertion mutation at position 738,739 show surprising and unexpected results as well. It was found that Klentaq 742RR (i.e., Klentaq having E742R and A743R substitutions) has RT-LAMP ability, although it exhibits a high, competing level of primer-dimer formation compared to Taq D732N. Also, it was observed that Bst DNA polymerase has a high and useful level of RT activity, so that it can carry out RT-LAMP in the PCR buffer that was used in these examples.

REFERENCES

1. Li, Y., Korolev, S. and Waksman, G. (1998) Crystal structures of open and closed forms of binary and ternary complexes of the large fragment of *Thermus aquaticus* DNA polymerase I: structural basis for nucleotide incorporation. The EMBO journal, 17, 7514-7525.
2. Tomita, N., Mori, Y., Kanda, H. and Notomi, T. (2008) Loop-mediated isothermal amplification (LAMP) of gene sequences and simple visual detection of products. Nature protocols, 3, 877-882.
3. Blatter, N., Bergen, K., Nolte, O., Welte, W., Diederichs, K., Mayer, J., Wieland, M. and Marx, A. (2013) Structure and Function of an RNA-Reading Thermostable DNA Polymerase. Angewandte Chemie International Edition, 52, 11935-11939.
4. Ong, J. L., Loakes, D., Jaroslawski, S., Too, K. and Holliger, P. (2006) Directed evolution of DNA polymerase, RNA polymerase and reverse transcriptase activity in a single polypeptide. Journal of molecular biology, 361, 537-550.

5. Barnes, W. M. (1994) PCR amplification of up to 35-kb DNA with high fidelity and high yield from lambda bacteriophage templates. Proceedings of the National Academy of Sciences, 91, 2216-2220.
6. Yamagami, T., Ishino, S., Kawarabayasi, Y. and Ishino, Y. (2014) Mutant Taq DNA polymerases with improved elongation ability as a useful reagent for genetic engineering. Frontiers in microbiology, 5.
7. Ignatov, K., Miroshnikov, A. and Kramarov, V. (1998) Substitution of Asn for Ser$^{543}$ in the large fragment of *Taq* DNA polymerase increases the efficiency of synthesis of long DNA molecules. FEBS letters, 425, 249-250.
8. Martin, B. R., Giepmans, B. N., Adams, S. R. and Tsien, R. Y. (2005) Mammalian cell-based optimization of the biarsenical-binding tetracysteine motif for improved fluorescence and affinity. Nature biotechnology, 23, 1308-1314.
9. Myers, T. W. and Gelfand, D. H. (1991) Reverse transcription and DNA amplification by a *Thermus thermophilus* DNA polymerase. Biochemistry, 30, 7661-7666.
10. Dieffenbach, C. W. and Dveksler, G. (1993) Setting up a PCR laboratory. Genome Research, 3, S2-S7.
11. Kermekchiev, M., Kirilova, L., Vail, E. and Barnes, W. (2009) Mutants of Taq DNA polymerase resistant to PCR inhibitors allow DNA amplification from whole blood and crude soil samples. Nucleic Acids Research, 37, e40.
12. Chandler et al. 2014 Frontiers in Microbiol., 5

SEQUENCE LISTING

```
Sequence total quantity: 32
SEQ ID NO: 1            moltype = AA  length = 832
FEATURE                 Location/Qualifiers
source                  1..832
                        mol_type = protein
                        organism = Thermus aquaticus
SEQUENCE: 1
MRGMLPLFEP KGRVLLVDGH HLAYRTFHAL KGLTTSRGEP VQAVYGFAKS LLKALKEDGD   60
AVIVVFDAKA PSFRHEAYGG YKAGRAPTPE DFPRQLALIK ELVDLLGLAR LEVPGYEADD  120
VLASLAKKAE KEGYEVRILT ADKDLYQLLS DRIHVLHPEG YLITPAWLWE KYGLRPDQWA  180
DYRALTGDES DNLPGVKGIG EKTARKLLEE WGSLEALLKN LDRLKPAIRE KILAHMDDLK  240
LSWDLAKVRT DLPLEVDFAK RREPDRERLR AFLERLEFGS LLHEFGLLES PKALEEAPWP  300
PPEGAFVGFV LSRKEPMWAD LLALAAARGG RVHRAPEPYK ALRDLKEARG LLAKDLSVLA  360
LREGLGLPPG DDPMLLAYLL DPSNTTPEGV ARRYGGEWTE EAGERAALSE RLFANLWGRL  420
EGEERLLWLY REVERPLSAV LAHMEATGVR LDVAYLRALS LEVAEEIARL EAEVFRLAGH  480
PFNLNSRDQL ERVLFDELGL PAIGKTEKTG KRSTSAAVLE ALREAHPIVE KILQYRELTK  540
LKSTYIDPLP DLIHPRTGRL HTRFNQTATA TGRLSSSDPN LQNIPVRTPL GQRIRRAFIA  600
EEGWLLVALD YSQIELRVLA HLSGDENLIR VFQEGRDIHT ETASWMFGVP REAVDPLMRR  660
AAKTINFGVL YGMSAHRLSQ ELAIPYEEAQ AFIERYFQSF PKVRAWIEKT LEEGRRRGYV  720
ETLFGRRRYV PDLEARVKSV REAAERMAFN MPVQGTAADL MKLAMVKLFP RLEEMGARML  780
LQVHDELVLE APKERAEAVA RLAKEVMEGV YPLAVPLEVE VGIGEDWLSA KE          832

SEQ ID NO: 2            moltype = AA  length = 554
FEATURE                 Location/Qualifiers
source                  1..554
                        mol_type = protein
                        organism = Thermus aquaticus
SEQUENCE: 2
MGLLHEFGLL ESPKALEEAP WPPPEGAFVG FVLSRKEPMW ADLLALAAAR GGRVHRAPEP   60
YKALRDLKEA RGLLAKDLSV LALREGLGLP PGDDPMLLAY LLDPSNTTPE GVARRYGGEW  120
TEEAGERAAL SERLFANLWG RLEGEERLLW LYREVERPLS AVLAHMEATG VRLDVAYLRA  180
LSLEVAEEIA RLEAEVFRLA GHPFNLNSRD QLERVLFDEL GLPAIGKTEK TGKRSTSAAV  240
LEALREAHPI VEKILQYREL TKLKSTYIDP LPDLIHPRTG RLHTRFNQTA TATGRLSSSD  300
PNLQNIPVRT PLGQRIRRAF IAEEGWLLVA LDYSQIELRV LAHLSGDKNL IRVFQEGRDI  360
HTETASWMFG VPREAVDPLM RRAAKTINFG VLYGMSAHRL SQELAIPYEE AQAFIERYFQ  420
SFPKVRAWLK KTLEEGRRRG YVETLFGRRR YVPDLEARVK SVREAAERMA FNMPVQGTAA  480
DLMKLAMVKL FPRLEEMGAR MLLQVHDELV LEAPKERAEA VARLAKEVME GVYPLAVPLE  540
VEVGIGEDWL SAKE                                                    554

SEQ ID NO: 3            moltype = AA  length = 832
FEATURE                 Location/Qualifiers
source                  1..832
                        mol_type = protein
                        organism = Thermus aquaticus
SEQUENCE: 3
MRGMLPLFEP KGRVLLVDGH HLAYRTFHAL KGLTTSRGEP VQAVYGFAKS LLKALKEDGD   60
AVIVVFDAKA PSFRHEAYGG YKAGRAPTPE DFPRQLALIK ELVDLLGLAR LEVPGYEADD  120
VLASLAKKAE KEGYEVRILT ADKDLYQLLS DRIHVLHPEG YLITPAWLWE KYGLRPDQWA  180
DYRALTGDES DNLPGVKGIG EKTARKLLEE WGSLEALLKN LDRLKPAIRE KILAHMDDLK  240
LSWDLAKVRT DLPLEVDFAK RREPDRERLR AFLERLEFGS LLHEFGLLES PKALEEAPWP  300
PPEGAFVGFV LSRKEPMWAD LLALAAARGG RVHRAPEPYK ALRDLKEARG LLAKDLSVLA  360
LREGLGLPPG DDPMLLAYLL DPSNTTPEGV ARRYGGEWTE EAGERAALSE RLFANLWGRL  420
EGEERLLWLY REVERPLSAV LAHMEATGVR LDVAYLRALS LEVAEEIARL EAEVFRLAGH  480
PFNLNSRDQL ERVLFDELGL PAIGKTEKTG KRSTSAAVLE ALREAHPIVE KILQYRELTK  540
LKSTYIDPLP DLIHPRTGRL HTRFNQTATA TGRLSSSDPN LQNIPVRTPL GQRIRRAFIA  600
EEGWLLVALD YSQIELRVLA HLSGDENLIR VFQEGRDIHT ETASWMFGVP REAVDPLMRR  660
AAKTINFGVL YGMSAHRLSQ ELAIPYEEAQ AFIERYFQSF PKVRAWIEKT LEEGRRRGYV  720
ETLFGRRRYV PNLEARVKSV REAAERMAFN MPVQGTAADL MKLAMVKLFP RLEEMGARML  780
LQVHDELVLE APKERAEAVA RLAKEVMEGV YPLAVPLEVE VGIGEDWLSA KE          832
```

```
SEQ ID NO: 4            moltype = AA  length = 554
FEATURE                 Location/Qualifiers
source                  1..554
                        mol_type = protein
                        organism = Thermus aquaticus
SEQUENCE: 4
MGLLHEFGLL ESPKALEEAP WPPPEGAFVG FVLSRKEPMW ADLLALAAAR GGRVHRAPEP    60
YKALRDLKEA RGLLAKDLSV LALREGLGLP PGDDPMLLAY LLDPSNTTPE GVARRYGGEW   120
TEEAGERAAL SERLFANLWG RLEGEERLLW LYREVERPLS AVLAHMEATG VRLDVAYLRA   180
LSLEVAEEIA RLEAEVFRLA GHPFNLNSRD QLERVLFDEL GLPAIGKTEK TGKRSTSAAV   240
LEALREAHPI VEKILQYREL TKLKSTYIDP LPDLIHPRTG RLHTRFNQTA TATGRLSSSD   300
PNLQNIPVRT PLGQRIRRAF IAEEGWLLVA LDYSQIELRV LAHLSGDKNL IRVFQEGRDI   360
HTETASWMFG VPREAVDPLM RRAAKTINFG VLYGMSAHRL SQELAIPYEE AQAFIERYFQ   420
SFPKVRAWLK KTLEEGRRRG YVETLFGRRR YVPNLEARVK SVREAAERMA FNMPVQGTAA   480
DLMKLAMVKL FPRLEEMGAR MLLQVHDELV LEAPKERAEA VARLAKEVME GVYPLAVPLE   540
VEVGIGEDWL SAKE                                                    554

SEQ ID NO: 5            moltype = AA  length = 832
FEATURE                 Location/Qualifiers
source                  1..832
                        mol_type = protein
                        organism = Thermus aquaticus
SEQUENCE: 5
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ARDLLAKDLS VLA           360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV RRRAERMAFN MPVQGTAADL MKLAMVKLFP RLEEMGARML   780
LQVHDELVLE APKERAEAVA RLAKEVMEGV YPLAVPLEVE VGIGEDWLSA KE           832

SEQ ID NO: 6            moltype = AA  length = 554
FEATURE                 Location/Qualifiers
source                  1..554
                        mol_type = protein
                        organism = Thermus aquaticus
SEQUENCE: 6
MGLLHEFGLL ESPKALEEAP WPPPEGAFVG FVLSRKEPMW ADLLALAAAR GGRVHRAPEP    60
YKALRDLKEA RGLLAKDLSV LALREGLGLP PGDDPMLLAY LLDPSNTTPE GVARRYGGEW   120
TEEAGERAAL SERLFANLWG RLEGEERLLW LYREVERPLS AVLAHMEATG VRLDVAYLRA   180
LSLEVAEEIA RLEAEVFRLA GHPFNLNSRD QLERVLFDEL GLPAIGKTEK TGKRSTSAAV   240
LEALREAHPI VEKILQYREL TKLKSTYIDP LPDLIHPRTG RLHTRFNQTA TATGRLSSSD   300
PNLQNIPVRT PLGQRIRRAF IAEEGWLLVA LDYSQIELRV LAHLSGDKNL IRVFQEGRDI   360
HTETASWMFG VPREAVDPLM RRAAKTINFG VLYGMSAHRL SQELAIPYEE AQAFIERYFQ   420
SFPKVRAWLK KTLEEGRRRG YVETLFGRRR YVPDLEARVK SVRRRAERMA FNMPVQGTAA   480
DLMKLAMVKL FPRLEEMGAR MLLQVHDELV LEAPKERAEA VARLAKEVME GVYPLAVPLE   540
VEVGIGEDWL SAKE                                                    554

SEQ ID NO: 7            moltype = AA  length = 832
FEATURE                 Location/Qualifiers
source                  1..832
                        mol_type = protein
                        organism = Thermus aquaticus
SEQUENCE: 7
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ARDLLAKDLS VLA           360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PNLEARVKSV RRRAERMAFN MPVQGTAADL MKLAMVKLFP RLEEMGARML   780
LQVHDELVLE APKERAEAVA RLAKEVMEGV YPLAVPLEVE VGIGEDWLSA KE           832

SEQ ID NO: 8            moltype = AA  length = 554
FEATURE                 Location/Qualifiers
```

```
source                  1..554
                        mol_type = protein
                        organism = Thermus aquaticus
SEQUENCE: 8
MGLLHEFGLL ESPKALEEAP WPPPEGAFVG FVLSRKEPMW ADLLALAAAR GGRVHRAPEP    60
YKALRDLKEA RGLLAKDLSV LALREGLGLP PGDDPMLLAY LLDPSNTTPE GVARRYGGEW   120
TEEAGERAAL SERLFANLWG RLEGEERLLW LYREVERPLS AVLAHMEATG VRLDVAYLRA   180
LSLEVAEEIA RLEAEVFRLA GHPFNLNSRD QLERVLFDEL GLPAIGKTEK TGKRSTSAAV   240
LEALREAHPI VEKILQYREL TKLKSTYIDP LPDLIHPRTG RLHTRFNQTA TATGRLSSSD   300
PNLQNIPVRT PLGQRIRRAF IAEEGWLLVA LDYSQIELRV LAHLSGDKNL IRVFQEGRDI   360
HTETASWMFG VPREAVDPLM RRAAKTINFG VLYGMSAHRL SQELAIPYEE AQAFIERYFQ   420
SFPKVRAWLK KTLEEGRRRG YVETLFGRRR YVPNLEARVK SVRRRAERMA FNMPVQGTAA   480
DLMKLAMVKL FPRLEEMGAR MLLQVHDELV LEAPKERAEA VARLAKEVME GVYPLAVPLE   540
VEVGIGEDWL SAKE                                                    554

SEQ ID NO: 9            moltype = AA  length = 563
FEATURE                 Location/Qualifiers
source                  1..563
                        mol_type = protein
                        organism = Thermus aquaticus
SEQUENCE: 9
MGLLHEFGLL ESPKALEEAP WPPPEGAFVG FVLSRKEPMW ADLLALAAAR GGRVHRAPEP    60
YKALRDLKEA RGLLAKDLSV LALREGLGLP PGDDPMLLAY LLDPSNTTPE GVARRYGGEW   120
TEEAGERAAL SERLFANLWG RLEGEERLLW LYREVERPLS AVLAHMEATG VRLDVAYLRA   180
LSLEVAEEIA RLEAEVFRLA GHPFNLNSRD QLERVLFDEL GLPAIGKTEK TGKRSTSAAV   240
LEALREAHPI VEKILQYREL TKLKSTYIDP LPDLIHPRTG RLHTRFNQTA TATGRLSSSD   300
PNLQNIPVRT PLGQRIRRAF IAEEGWLLVA LDYSQIELRV LAHLSGDKNL IRVFQEGRDI   360
HTETASWMFG VPREAVDPLM RRAAKTINFG VLYGMSAHRL SQELAIPYEE AQAFIERYFQ   420
SFPKVRAWLK KTLEEGRRRG YVETLFGRRR YVPNLEARVK FLNCCPGCCS VRRRAERMAF   480
NMPVQGTAAD LMKLAMVKLF PRLEEMGARM LLQVHDELVL EAPKERAEAV ARLAKEVMEG   540
VYPLAVPLEV EVGIGEDWLS AKE                                          563

SEQ ID NO: 10           moltype = AA  length = 581
FEATURE                 Location/Qualifiers
source                  1..581
                        mol_type = protein
                        organism = Bacillus stearothermophilus
SEQUENCE: 10
MAKMAFTLAD RVTEEMLADK AALVVEVVEE NYHDAPIVGI AVVNEHGRFF LRPETALADP    60
QFVAWLGDET KKKSMFDSKR AAVALKWKGI ELCGVSFDLL LAAYLLDPAQ GVDDVAAAAK   120
MKQYEAVRPD EAVYGKGAKR AVPDEPVLAE HLVRKAAAIW ELERPFLDEL RRNEQDRLLV   180
ELEQPLSSIL AEMEFAGVKV DTKRLEQMGK ELAEQLGTVE QRIYELAGQE FNINSPKQLG   240
VILFEKLQLP VLKKTKTGYS TSADVLEKLA PYHEIVENIL HYRQLGKLQS TYIEGLLKVV   300
RPDTKKVHTI FNQALTQTGR LSSTEPNLQN IPIRLEEGRK IRQAFVPSES DWLIFAADYS   360
QIELRVLAHI AEDDNLMEAF RRDLDIHTKT AMDIFQVSED EVTPNMRRQA KAVNFGIVYG   420
ISDYGLAQNL NISRKEAAEF IERYFESFPG VKRYMENIVQ EAKQKGYVTT LLHRRRYLPD   480
ITSRNFNVRS FAERMAMNTP IQGSAADIIK KAMIDLNARL KEERLQAHLL LQVHDELILE   540
APKEEMERLC RLVPEVMEQA VTLRVPLKVD YHYGSTWYDA K                      581

SEQ ID NO: 11           moltype = DNA  length = 31
FEATURE                 Location/Qualifiers
misc_feature            1..31
                        note = PCR Primer
source                  1..31
                        mol_type = other DNA
                        organism = synthetic construct
SEQUENCE: 11
tacagacgtt taagcttcgc aattaccggt t                                  31

SEQ ID NO: 12           moltype = DNA  length = 30
FEATURE                 Location/Qualifiers
misc_feature            1..30
                        note = PCR Primer
source                  1..30
                        mol_type = other DNA
                        organism = synthetic construct
SEQUENCE: 12
aaaaagctgc aaattgcggt aggtattatt                                    30

SEQ ID NO: 13           moltype = DNA  length = 28
FEATURE                 Location/Qualifiers
misc_feature            1..28
                        note = PCR Primer
source                  1..28
                        mol_type = other DNA
                        organism = synthetic construct
SEQUENCE: 13
ctaccaaggt aatgaagcaa atggatat                                      28
```

```
SEQ ID NO: 14              moltype = DNA  length = 27
FEATURE                    Location/Qualifiers
misc_feature               1..27
                           note = PCR Primer
source                     1..27
                           mol_type = other DNA
                           organism = synthetic construct
SEQUENCE: 14
tggcagcaac caaagtatat gaaaggg                                            27

SEQ ID NO: 15              moltype = DNA  length = 26
FEATURE                    Location/Qualifiers
misc_feature               1..26
                           note = PCR Primer
source                     1..26
                           mol_type = other DNA
                           organism = synthetic construct
SEQUENCE: 15
ggcattgttt ggtaggtgag agatct                                             26

SEQ ID NO: 16              moltype = DNA  length = 30
FEATURE                    Location/Qualifiers
misc_feature               1..30
                           note = PCR Primer
source                     1..30
                           mol_type = other DNA
                           organism = synthetic construct
SEQUENCE: 16
acaaatgaca agagtctggt tcagaagata                                         30

SEQ ID NO: 17              moltype = DNA  length = 74
FEATURE                    Location/Qualifiers
misc_feature               1..74
                           note = Stem-loop
source                     1..74
                           mol_type = other DNA
                           organism = synthetic construct
SEQUENCE: 17
agctctgtct cttatacaca tctaatagtt taactttaag aaggagatat aaataagatg        60
tgtataagag acag                                                          74

SEQ ID NO: 18              moltype = DNA  length = 20
FEATURE                    Location/Qualifiers
misc_feature               1..20
                           note = RT-LAMP Primer
source                     1..20
                           mol_type = other DNA
                           organism = synthetic construct
SEQUENCE: 18
tgtcatggga tccggatgtt                                                    20

SEQ ID NO: 19              moltype = DNA  length = 20
FEATURE                    Location/Qualifiers
misc_feature               1..20
                           note = RT-LAMP Primer
source                     1..20
                           mol_type = other DNA
                           organism = synthetic construct
SEQUENCE: 19
caatagagcc gctctcagag                                                    20

SEQ ID NO: 20              moltype = DNA  length = 19
FEATURE                    Location/Qualifiers
misc_feature               1..19
                           note = RT-LAMP Primer
source                     1..19
                           mol_type = other DNA
                           organism = synthetic construct
SEQUENCE: 20
ccagagagga ggttgccaa                                                     19

SEQ ID NO: 21              moltype = DNA  length = 19
FEATURE                    Location/Qualifiers
misc_feature               1..19
                           note = RT-LAMP Primer
source                     1..19
                           mol_type = other DNA
                           organism = synthetic construct
SEQUENCE: 21
```

-continued

```
tgcaggatgc agcgcctta                                                    19

SEQ ID NO: 22          moltype = DNA   length = 46
FEATURE                Location/Qualifiers
misc_feature           1..46
                       note = RT-LAMP Primer
source                 1..46
                       mol_type = other DNA
                       organism = synthetic construct
SEQUENCE: 22
gcccaaacaa cgacgatcgg tagagtcaaa ccagcatccg tagcct                      46

SEQ ID NO: 23          moltype = DNA   length = 45
FEATURE                Location/Qualifiers
misc_feature           1..45
                       note = RT-LAMP Primer
source                 1..45
                       mol_type = other DNA
                       organism = synthetic construct
SEQUENCE: 23
gcacgttctc caacggtgct gagtcggttg cttgttcagc gaact                       45

SEQ ID NO: 24          moltype = DNA   length = 22
FEATURE                Location/Qualifiers
misc_feature           1..22
                       note = PCR Primer
source                 1..22
                       mol_type = other DNA
                       organism = synthetic construct
SEQUENCE: 24
agggtgcata tgagatgctt ac                                                22

SEQ ID NO: 25          moltype = DNA   length = 22
FEATURE                Location/Qualifiers
misc_feature           1..22
                       note = PCR Primer
source                 1..22
                       mol_type = other DNA
                       organism = synthetic construct
SEQUENCE: 25
agatacctag agacgacaac ca                                                22

SEQ ID NO: 26          moltype = DNA   length = 21
FEATURE                Location/Qualifiers
misc_feature           1..21
                       note = PCR Primer
source                 1..21
                       mol_type = other DNA
                       organism = synthetic construct
SEQUENCE: 26
gatcgtatcc gctcacacta c                                                 21

SEQ ID NO: 27          moltype = DNA   length = 23
FEATURE                Location/Qualifiers
misc_feature           1..23
                       note = PCR Primer
source                 1..23
                       mol_type = other DNA
                       organism = synthetic construct
SEQUENCE: 27
tgcaatctca ctgggacata taa                                               23

SEQ ID NO: 28          moltype = DNA   length = 20
FEATURE                Location/Qualifiers
misc_feature           1..20
                       note = RT-LAMP Primer
source                 1..20
                       mol_type = other DNA
                       organism = synthetic construct
SEQUENCE: 28
gtaaaaacac ctcacgagtt                                                   20
```

```
SEQ ID NO: 29          moltype = DNA  length = 21
FEATURE                Location/Qualifiers
misc_feature           1..21
                       note = RT-LAMP Primer
source                 1..21
                       mol_type = other DNA
                       organism = synthetic construct
SEQUENCE: 29
tttacgaaca ttaagcgact t                                              21

SEQ ID NO: 30          moltype = DNA  length = 45
FEATURE                Location/Qualifiers
misc_feature           1..45
                       note = RT-LAMP Primer
source                 1..45
                       mol_type = other DNA
                       organism = synthetic construct
SEQUENCE: 30
tcctacggtc aagagaagca ataaacacct aagttctcac cgaat                    45

SEQ ID NO: 31          moltype = DNA  length = 40
FEATURE                Location/Qualifiers
misc_feature           1..40
                       note = RT-LAMP Primer
source                 1..40
                       mol_type = other DNA
                       organism = synthetic construct
SEQUENCE: 31
ctttccacat gcaggatttt ggatgcacgc aatggtgtag                          40

SEQ ID NO: 32          moltype = AA  length = 9
FEATURE                Location/Qualifiers
REGION                 1..9
                       note = FlAsH insertion peptide
source                 1..9
                       mol_type = protein
                       organism = synthetic construct
SEQUENCE: 32
FLNCCPGCC                                                            9
```

The invention claimed is:

1. A method of synthesizing a complementary DNA (cDNA) in a reverse transcriptase reaction comprising:
   forming an assay mixture comprising
   (A) a sample comprising a target RNA,
   (B) a primer which anneals to the target RNA,
   (C) a buffer, and
   (D) at least one mutant polymerase comprising a polypeptide sequence having
      (i) at least 95% sequence identity to SEQ ID NO: 1 or SEQ ID NO: 2,
      (ii) reverse transcriptase activity and DNA polymerase activity, and
      (iii) a D732N substitution according to the numbering of wild type Taq polymerase of SEQ ID NO: 1, wherein the assay mixture does not include a separate reverse transcriptase enzyme in an amount sufficient to generate cDNA from the target RNA or in an amount sufficient to initiate reverse transcription of the target RNA; and
   allowing reverse transcription of the target RNA to synthesize the cDNA in the assay mixture, wherein the assay mixture does not include a separate reverse transcriptase enzyme in an amount sufficient to generate cDNA from the target RNA or in an amount sufficient to initiate reverse transcription of the target RNA.

2. The method of claim 1, wherein the assay mixture does not include $Mn^{++}$ ion.

3. The method of claim 1, wherein the sample comprising a target RNA is not purified prior to addition to the assay mixture.

4. A method of amplifying a target nucleic acid in a reverse transcriptase loop-mediated isothermal amplification (RT-LAMP) comprising:
   forming an assay mixture comprising
   (A) a sample comprising the target nucleic acid, wherein the target nucleic acid is a target RNA,
   (B) four or six LAMP primers, wherein at least one primer anneals to the target RNA and wherein the four to six LAMP primers anneal to the cDNA or DNA synthesized therefrom,
   (C) a buffer, and
   (D) at least one mutant polymerase comprising a polypeptide sequence having
      (a) at least 95% sequence identity to SEQ ID NO: 1 or SEQ ID NO:2,
      (b) DNA polymerase activity, reverse transcriptase activity, and strand displacement activity, and
      (c) a D732N substitution according to the numbering of wild type Taq polymerase of SEQ ID NO: 1, wherein the assay mixture does not include a separate reverse transcriptase enzyme in an amount sufficient to generate cDNA from the target RNA or in an amount sufficient to initiate reverse transcription of the target RNA; and
   amplifying the target nucleic acid in the assay mixture in RT-LAMP, wherein the assay mixture for the amplifying does not include a separate reverse transcriptase enzyme in an amount sufficient to generate cDNA from the target RNA or in an amount sufficient to initiate reverse transcription of the target RNA.

5. The method of claim 4, wherein the assay mixture does not include $Mn^{++}$ ion.

6. The method of claim 4, wherein the sample comprising the target nucleic acid is not purified prior to addition to the assay mixture.

7. The method of claim 4, wherein the assay mixture comprises an inhibitory substance in an amount sufficient to cause a wild type Taq polymerase to fail to amplify the target nucleic acid in the RT-LAMP.

8. The method of claim 7, wherein the inhibitory substance comprises whole blood, a blood traction, chocolate, peanut buffer, milk, seafood, meat, egg, or a soil extract.

9. The method of claim 4, wherein the at least one mutant polymerase comprises a polypeptide sequence selected from the group consisting of SEQ ID NO: 3, SEQ ID NO: 4, SEQ ID NO: 5, SEQ ID NO: 6, SEQ ID NO: 7; SEQ ID NO: 8, or SEQ ID NO: 9, or a variant thereof having at least 95% sequence identity thereto and (A) DNA polymerase activity, (B) strand displacement activity, and (C) reverse transcriptase activity.

10. The method of claim 4, wherein the at least one mutant polymerase further comprises at least one mutation selected from the group consisting of L609P, E626K, V649I, I707L, E708K, E708L, E708N, E708Q, E708I, E708W, E708R, E708V, E708S, E404G, G418E, V453L, A454S, R487G, I528M, L533R, D551G, D578E, I599V, L657Q, K738R, L781I, and E818V according to the numbering of wild type Taq polymerase of SEQ ID NO: 1.

11. The method of claim 4, wherein the at least one mutant polymerase comprises a polypeptide sequence having at least 95% sequence identity to SEQ ID NO: 2.

12. The method of claim 11, wherein the at least one mutant polymerase further comprises substitutions E742R and A743R.

13. The method of claim 4, wherein the at least one mutant polymerase further comprises at least one substitution selected from the group consisting of D119A, D119N, E742R, and A743R according to the numbering of wild type Taq polymerase of SEQ ID NO: 1.

14. The method of claim 1, wherein the at least one mutant polymerase comprises a polypeptide sequence having at least 95% sequence identity to SEQ ID NO: 1.

15. The method of claim 13, wherein the at least one mutant polymerase comprises substitutions E742R and A743R.

* * * * *